(12) United States Patent
Hough et al.

(10) Patent No.: US 8,784,786 B2
(45) Date of Patent: *Jul. 22, 2014

(54) RHEOLOGY MODIFIER POLYMER

(75) Inventors: Lawrence Hough, Philadelphia, PA (US); Wojciech Bzducha, Lyons (FR); Pascal Herve, West Windsor, NJ (US); Pierre Hennaux, New York, NY (US); Andrew Douglass, Pleasanton, CA (US); Monique Adamy, Paris (FR); Inigo Gonzalez, Paris (FR)

(73) Assignee: Rhodia Operations, Ambervilliers (FR)

( * ) Notice: Subject to any disclaimer, the term of this patent is extended or adjusted under 35 U.S.C. 154(b) by 326 days.

This patent is subject to a terminal disclaimer.

(21) Appl. No.: 12/931,903

(22) Filed: Feb. 14, 2011

(65) Prior Publication Data

US 2011/0243873 A1    Oct. 6, 2011

Related U.S. Application Data

(60) Provisional application No. 61/337,927, filed on Feb. 12, 2010.

(51) Int. Cl.
*A61Q 5/06* (2006.01)
*A61K 47/32* (2006.01)
*C08F 24/00* (2006.01)
*C08F 124/00* (2006.01)
*C08F 224/00* (2006.01)

(52) U.S. Cl.
USPC .............. 424/70.16; 514/772.4; 526/273

(58) Field of Classification Search
CPC ..... A61Q 19/00; A61Q 19/10; A61K 8/8152; C08F 220/28; C07C 69/54
USPC ............ 424/70.16; 526/273; 514/772.4; 510/434; 252/188.1
See application file for complete search history.

(56) References Cited

U.S. PATENT DOCUMENTS

| | | | |
|---|---|---|---|
| 2,458,888 A | 1/1949 | Rehberg et al. | |
| 3,035,004 A | 5/1962 | Glavis | |
| 3,652,497 A | 3/1972 | Junas et al. | |
| 3,937,283 A | 2/1976 | Blauer et al. | |
| 4,138,381 A | 2/1979 | Chang et al. | |
| 4,351,754 A | 9/1982 | Dupre | |
| 4,384,096 A | 5/1983 | Sonnabend | |
| 4,579,670 A | 4/1986 | Payne | |
| 4,620,028 A | 10/1986 | Gorman et al. | |
| 4,668,410 A | 5/1987 | Haas et al. | |
| 4,734,099 A | 3/1988 | Cyprien | |
| 4,830,769 A | 5/1989 | O'Lenick et al. | |
| 4,892,916 A | 1/1990 | Hawe et al. | |
| 5,104,643 A | 4/1992 | Grollier et al. | |
| 5,292,843 A | 3/1994 | Jenkins et al. | |
| 5,294,693 A | 3/1994 | Egraz et al. | |
| 5,415,860 A | 5/1995 | Beucherie et al. | |
| 5,551,516 A | 9/1996 | Norman et al. | |
| 5,607,680 A | 3/1997 | Brissonnet et al. | |
| 5,674,823 A | 10/1997 | Ricca et al. | |
| 5,686,024 A | 11/1997 | Dahanayake et al. | |
| 5,853,710 A | 12/1998 | Dehan et al. | |
| 5,858,343 A | 1/1999 | Szymczak | |
| 5,874,495 A | 2/1999 | Robinson et al. | |
| 5,902,574 A | 5/1999 | Stoner et al. | |
| 5,902,778 A | 5/1999 | Hartmann et al. | |
| 6,150,312 A | 11/2000 | Puvvada et al. | |
| 6,162,877 A | 12/2000 | Sau | |
| 6,433,061 B1 | 8/2002 | Marchant | |
| 6,846,798 B2 | 1/2005 | Joye et al. | |
| 6,897,253 B2 | 5/2005 | Schmucker-Castner et al. | |
| 7,217,752 B2 | 5/2007 | Schmucker-Castner et al. | |
| 7,288,616 B2 | 10/2007 | Tamareselvy et al. | |
| 7,378,479 B2 | 5/2008 | Tamareselvy et al. | |
| 7,772,421 B2 | 8/2010 | Yang et al. | |
| 8,071,674 B2 * | 12/2011 | Yang et al. | 524/502 |
| 2003/0180246 A1 | 9/2003 | Frantz et al. | |
| 2003/0190302 A1 | 10/2003 | Frantz et al. | |
| 2004/0247549 A1 | 12/2004 | Lu et al. | |
| 2005/0002892 A1 | 1/2005 | Khan et al. | |
| 2005/0175568 A1 | 8/2005 | Asari et al. | |
| 2006/0040837 A1 | 2/2006 | Frantz et al. | |
| 2006/0135627 A1 | 6/2006 | Frantz et al. | |
| 2006/0135683 A1 | 6/2006 | Adam | |
| 2006/0270563 A1 * | 11/2006 | Yang et al. | 507/119 |
| 2008/0095733 A1 | 4/2008 | Griffin et al. | |
| 2011/0223125 A1 | 9/2011 | Hough et al. | |
| 2012/0116005 A1 | 5/2012 | Yang et al. | |
| 2012/0116040 A1 | 5/2012 | Yang et al. | |
| 2012/0121523 A1 | 5/2012 | Yang et al. | |
| 2012/0123149 A1 | 5/2012 | Yang et al. | |

FOREIGN PATENT DOCUMENTS

| | | |
|---|---|---|
| DE | 3822202 A1 | 1/1998 |
| EP | 226097 B1 | 5/1990 |
| EP | 705852 B1 | 12/1998 |
| EP | 1949888 A1 | 7/2008 |
| WO | 98/41505 A1 | 9/1998 |

OTHER PUBLICATIONS

C.E. Rehberg, et al., "Preparation and Properties of Monomeric and Polymeric Acrylic Esters of Ether-Alcohols," Journal of Organic Chemistry, vol. 14, 1949, pp. 1094-1098, XP002594784.

(Continued)

*Primary Examiner* — Blessing M Fubara

(57) ABSTRACT

A polymer includes (a) one or more first monomeric units, each independently comprising at least one bicycloheptyl-polyether, bicycloheptenyl-polyether or branched ($C_5$-$C_{50}$) alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom, and (b) one or more second monomeric units, each independently comprising at least one pendant linear or branched ($C_5$-$C_{50}$)alkyl-polyether group per monomeric unit, provided that the first and second monomeric units cannot both comprise a branched ($C_5$-$C_{50}$)alkyl-polyether group and is useful as a component in liquid compositions, such as aqueous latex coating compositions, personal care compositions, home care compositions, and institutional or industrial care compositions.

37 Claims, No Drawings

(56) References Cited

OTHER PUBLICATIONS

Jarchem Industries, Inc., Specialty Monomers, Acrylamides Methacrylates Acrylates others, brochure (2004).
Johansson (Specialty Chemicals Magazine, Nov. 2004: online at URL:<http://www.firp.ula.ve/archivos/material_web_4xx/04_SCM_Johansson.pdf>).
Office Action of Apr. 12, 2012 for U.S. Appl. No. 13/373,162 to Yang et al, filed Nov. 7, 2011.
Office Action of May 2, 2012 for U.S. Appl. No. 13/317,948 to Yang et al, filed Nov. 1, 2011.
STN Search Results (Apr. 5, 2012) listed in Notice of References Cited of Office Action of Apr. 12, 2012 for U.S. Appl. No. 13/373,162 to Yang et al, filed Nov. 7, 2011.
U.S. Appl. No. 13/728,434 to Yang et al, filed Dec. 27, 2012 (unpublished).
Jarchem, , URL:<http://www.jarchem.com/monomers/acrylate_mono.htm>, 2003, retrieved from the Internet via URL:<http://web.archive.org> (WaybackMachine webpage) Aug. 13, 2012.
Office Action of May 22, 2013 from U.S. Appl. No. 13/026,686 to Hough et al, filed Feb. 14, 2011.
Notice of Allowance of Apr. 15, 2013 from U.S. Appl. No. 13/317,948 to Yang et al, filed Nov. 1, 2011.
Notice of Allowance of Apr. 19, 2013 from U.S. Appl. No. 13/373,162 to Yang et al, filed Nov. 7, 2011.
Notice of Allowance of Apr. 16, 2013 from U.S. Appl. No. 13/373,154 to Yang et al, filed Nov. 7, 2011.
Notice of Allowance of Apr. 15, 2013 from U.S. Appl. No. 13/373,170 to Yang et al, filed Nov. 7, 2011.
Notice of Allowance of May 14, 2013 from U.S. Appl. No. 13/728,434 to Yang et al, filed Dec. 27, 2012.
May 6, 2014, Office Action for U.S. Appl. No. 13/026,686, Lawrence Alan Hough et al. filed Feb. 14, 2011.
Office Action of Aug. 6, 2013 from U.S. Appl. No. 13/026,686 to Hough et al filed Feb. 14, 2011.

\* cited by examiner

US 8,784,786 B2

RHEOLOGY MODIFIER POLYMER

This application claims the benefit of U.S. Provisional Application Ser. No. 61/337,927, filed Feb. 12, 2010.

FIELD OF THE INVENTION

The present invention relates to a rheology modifier polymer for use in liquid media, more typically aqueous media.

BACKGROUND

Liquid synthetic rheology modifier polymers typically fall within one of three categories: alkali-soluble or alkali-swellable emulsion ("ASE") polymers, hydrophobically modified alkali-soluble or alkali-swellable emulsion ("HASE") polymers, and hydrophobically modified ethoxylated urethane ("HEUR") polymers.

HASE and ASE polymers are generally known, see, for example those described in, U.S. Pat. No. 3,035,004, U.S. Pat. No. 5,292,843, U.S. Pat. No. 6,897,253, U.S. Pat. No. 7,288,616, U.S. Pat. No. 7,378,479, and US Patent Publication No. 2006/0270563, and have each been widely used as rheology modifiers in aqueous systems. However, some HASE polymers have shown deficiencies with respect to thickening efficiency, such as undesirably high sensitivity to relatively small variations in pH, electrolyte concentration, and the amount of polymer used. The thickening efficiency of such polymers in aqueous media tends to be low at low polymer concentration, for example, less than about 1% by weight polymer, particularly at low pH, such as for example, pH of less than about 6, but tends to markedly increase at higher polymer concentrations and/or higher pH. This sensitivity can lead to undesirably large changes in rheological properties, such as very dramatically increased viscosity, with relatively small changes in pH or polymer concentration. The disproportionately large changes in properties can lead to difficulty in designing a composition that has and maintains a desired performance profile under anticipated conditions of use, as well as to difficulties in manufacturing and handling such compositions. Cross-linked ASE polymers have also shown deficiencies with respect to thickening efficiency and thus may, particularly at low pH, require an undesirably large amount of polymer to provide the desired level of thickening, and, when used in an amount sufficient to provide the desired rheological properties, may impart a cloudy, translucent, or opaque visual appearance to aqueous compositions. A cloudy, translucent, or opaque visual appearance may be undesirable in end uses in which aesthetic criteria are important such as, for example, in personal care formulations, such as shampoos and body washes. Furthermore, some HASE and ASE polymers, such as some crosslinked alkali-swellable acrylate copolymers, typically exhibit a lower thickening efficiency and/or impart a cloudy, translucent or opaque visual appearance in the presence of salts and surfactants, which also limits the usefulness of such polymers in some systems, such as for example, personal care compositions.

There is an ongoing unresolved need for an associative polymer for use in modifying the rheological properties of liquid media, more typically aqueous media, that provides improved rheological, aesthetic, and/or application performance properties in such media.

SUMMARY OF THE INVENTION

In a first aspect, the present invention is directed to a polymer comprising:

(a) one or more first monomeric units, each independently comprising at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom, and (b) one or more second monomeric units, each independently comprising at least one pendant linear or branched ($C_5$-$C_{50}$)alkyl-polyether group per monomeric unit, provided that the first and second monomeric units cannot both comprise a branched ($C_5$-$C_{50}$)alkyl-polyether group.

The polymer typically has a weight average molecular weight of greater than or equal to about 30,000 grams per mole.

In one embodiment, the polymer is the product of copolymerization of a mixture of monomers, comprising:

(a) one or more first monomers, each independently selected from monomers that comprise a reactive functional group and at least one bicycloheptyl-polyether, bicycloheptenyl-polyether, or branched ($C_5$-$C_{50}$)alkyl-polyether group per molecule, wherein the bicycloheptyl-polyether or bicycloheptenyl-polyether group may optionally be substituted on one or more ring carbon atoms by one or two ($C_1$-$C_6$)alkyl groups per carbon atom, and (b) one or more second monomers, each independently selected from monomers that comprise a reactive functional group and at least one pendant straight or branched ($C_5$-$C_{50}$)alkyl-polyether group per molecule and that are copolymerizable with the first monomer, provided that the first and second monomers cannot both comprise a branched ($C_5$-$C_{50}$)alkyl-polyether group.

In a second aspect, the present invention is directed to a process for making a rheology modifier polymer comprising polymerizing a mixture of monomers that comprises:

(a) one or more first monomers, each independently selected from monomers that comprise a reactive functional group and at least one bicycloheptyl-polyether, bicycloheptenyl-polyether, or branched ($C_5$-$C_{50}$)alkyl-polyether group per molecule, wherein the bicycloheptyl-polyether or bicycloheptenyl-polyether group may optionally be substituted on one or more ring carbon atoms by one or two ($C_1$-$C_6$)alkyl groups per carbon atom, and (b) one or more second monomers, each independently selected from monomers that comprise a reactive functional group and at least one pendant straight or branched ($C_5$-$C_{50}$)alkyl-polyether group per molecule and that are copolymerizable with the first monomer, provided that the first and second monomers cannot both comprise a branched ($C_5$-$C_{50}$)alkyl-polyether group.

In a third aspect, the present invention is directed to a composition comprising a liquid medium, more typically water, and one or more polymers according to the present invention. In one embodiment, the composition further comprises one or more surfactants.

In one embodiment, the composition is an aqueous latex coating composition comprising water, a polymer according to the present invention, and a latex polymer.

In one embodiment, the composition is a personal care composition comprising water and a polymer according to the present invention, and, more typically, further comprising one or more surfactants.

In one embodiment, the composition is home care composition or institutional or industrial care composition comprising water and a polymer according to the present invention, and, more typically, further comprising one or more surfactants, and optionally further comprising one or more additives selected from builders, bleaching agents, acids, bases, or abrasives, antibacterial agents, fungicides, enzymes, and opacifying agents.

The polymer of the present invention is useful for modifying the rheological properties of an aqueous compositions and typically provide thickening and impart a non-zero yield strength to such compositions. In one embodiment, the polymer of the present invention provides thickening and imparts a non-zero yield strength to such compositions more efficiently, that is, at a lower total amount of polymer, than an analogous polymer blend provides thickening and imparts a yield strength to such compositions, wherein such analogous polymer blend is a blend of a first polymer that comprises the above described first monomeric units, but lacking the above described second monomeric units, with a second polymer that comprises the above described second monomeric units, but lacking the above described first monomeric units, and wherein the first and the second polymers of the blend each have a weight average molecular weight that is similar, that is within the range of plus or minus 25%, more typically plus or minus 10%, of the weight average molecular weight of the polymer of the present invention.

The performance polymer of the present invention has improved tolerance to salt content and surfactant content compared to typical HASE or ASE polymers in regard to thickening efficiency and/or visual clarity. Personal care compositions containing the polymer of the present invention typically exhibit good foam properties and good sensory properties and the polymer is easily rinsed with water from the skin or hair.

The polymer of the present invention is useful in, for example, personal care applications, such as, for example, shampoos, body wash, hand soap, lotions, creams, conditioners, shaving products, facial washes, neutralizing shampoos, personal wipes, and skin treatments, and in home care or institutional or industrial care applications, such as, for example, liquid detergents, laundry detergents, hard surface cleansers, dish wash liquids, toilet bowl cleaners, as well as other applications, such as oil field and agrochemical applications.

DETAILED DESCRIPTION OF THE INVENTION

The term "personal care composition" as used herein means compositions, including but not limited to cosmetics, toiletries, cosmeceuticals, beauty aids, personal hygiene and cleansing compositions for application to the body, including the skin, hair, scalp, and nails, of humans and animals. The term "health care compositions" as used herein means compositions including but not limited to pharmaceuticals, pharmacosmetics, oral (mouth and teeth) care compositions, such as oral suspensions, mouthwashes, toothpastes, and the like, and over-the-counter compositions for external application to the body, including the skin, scalp, nails, and mucous membranes of humans and animals, for ameliorating a health-related or medical condition, or for generally maintaining hygiene or well-being. The term "home care compositions" as used herein means compositions including, but not limited to, compositions for use in a domestic household for surface cleaning or maintaining sanitary conditions, such as in the kitchen and bathroom, and laundry products for fabric care and cleaning, and the like. The term "institutional and industrial care compositions" as used herein means compositions, including but not limited to, cleaning compositions, for use in surface cleaning or maintaining sanitary conditions in institutional and industrial environments, and compositions for treating textiles.

As used herein, the term "rheology" refers to the study of the flow and deformation behavior materials and the term "rheological properties" as used herein in reference to a material or composition means the flow and deformation properties of such material or composition, including viscosity, increase or decrease-in viscosity in response to shear stress or time, flow characteristics, gel properties such as stiffness, resilience, flowability, foam properties, such as foam stability, foam density, ability to hold a peak, and aerosol properties such as ability to form aerosol droplets when dispensed from propellant-based or mechanical pump-type aerosol dispensers. The term "aesthetic properties" as used herein in reference to a material or composition means the visual and tactile psychosensory properties, such as color, clarity, smoothness, tack, lubricity, texture, of such material or composition.

As used herein, the terminology "$(C_x-C_y)$" in reference to an organic group, wherein x and y are each integers, indicates that the group may contain from x carbon atoms to y carbon atoms per group.

As used herein, the term "alkyl" means a monovalent straight or branched saturated hydrocarbon radical, more typically, a monovalent straight or branched saturated $(C_1-C_{40})$hydrocarbon radical, such as, for example, methyl, ethyl, n-propyl, isopropyl, n-butyl, isobutyl, tert-butyl, hexyl, octyl, hexadecyl, octadecyl, eicosyl, behenyl, tricontyl, and tertacontyl.

As used herein, the term "cycloalkyl" means a saturated hydrocarbon radical, more typically a saturated $(C_5-C_{22})$ hydrocarbon radical, that includes one or more cyclic alkyl rings, which may optionally be substituted on one or more carbon atoms of the ring with one or two $(C_1-C_6)$alkyl groups per carbon atom, such as, for example, cyclopentyl, cycloheptyl, cyclooctyl, and "bicyloalkyl" means a cycloalkyl ring system that comprises two condensed rings, such as bicycloheptyl.

As used herein, the term "hydroxyalkyl" means an alkyl radical, more typically a $(C_1-C_{22})$alkyl radical, that is substituted with one or more hydroxyl groups, such as for example, hydroxymethyl, hydroxyethyl, hydroxypropyl, and hydroxydecyl.

As used herein, the term "alkoxyalkyl" means an alkyl radical that is substituted with one or more alkoxy substituents, more typically a $(C_1-C_{22})$alkyloxy-$(C_1-C_6)$alkyl radical, such as methoxymethyl, and ethoxybutyl.

As used herein, the term "alkenyl" means an unsaturated straight or branched hydrocarbon radical, more typically an unsaturated straight, branched, $(C_2-C_{22})$ hydrocarbon radical, that contains one or more carbon-carbon double bonds, such as, for example, ethenyl, n-propenyl, iso-propenyl, As used herein, the term "cycloalkenyl" means an unsaturated hydrocarbon radical, typically an unsaturated $(C_5-C_{22})$ hydrocarbon radical, that contains one or more cyclic alkenyl rings and which may optionally be substituted on one or more carbon atoms of the ring with one or two $(C_1-C_6)$alkyl groups per carbon atom, such as cyclohexenyl, cycloheptenyl, and "bicycloalkenyl" means a cycloalkenyl ring system that comprises two condensed rings, such as bicycloheptenyl.

The "bicyclo[d.e.f]" notation is used herein in reference to bicycloheptyl and bicycloheptenyl ring systems in accordance with the von Baeyer system for naming polycyclic compounds, wherein a bicyclic system is named by the prefix "bicyclo-" to indicate number of rings in the system, followed by a series of three arabic numbers, listed in descending numerical order, separated by full stops, and enclosed in square brackets, to indicate the respective number of skeletal atoms in each acyclic chain connecting the two common atoms (the "bridgehead atoms"), excluding the bridgehead atoms.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkoxyl, alkenyl, halo, haloalkyl, monocyclic aryl, or amino, such as, for example, phenyl, methylphenyl, methoxyphenyl, dimethylphenyl, trimethylphenyl, chlorophenyl, trichloromethylphenyl, triisobutyl phenyl, tristyrylphenyl, and aminophenyl.

As used herein, the term "aralkyl" means an alkyl group substituted with one or more aryl groups, more typically a $(C_1-C_{18})$alkyl substituted with one or more $(C_6-C_{14})$aryl substituents, such as, for example, phenylmethyl, phenylethyl, and triphenylmethyl.

As used herein the term "(meth)acrylate" refers collectively and alternatively to the acrylate and methacrylate and the term "(meth)acrylamide" refers collectively and alternatively to the acrylamide and methacrylamide, so that, for example, "butyl(meth)acrylate" means butyl acrylate and/or butyl methacrylate.

As used herein, "parts by weight" or "pbw" in reference to a named compound or material means the amount of the respective named compound or material, exclusive, for example, of any associated solvent. In some instances, the trade name of the commercial source of the compound is also given, typically in parentheses. For example, a reference to "10 pbw cocoamidopropyl betaine ("CAPB", as Mirataine BET C-30)" means 10 pbw of the actual betaine compound, added in the form of a commercially available aqueous solution of the betaine compound having the trade name "Mirataine BET C-30", and exclusive of the water contained in the aqueous solution. Alternatively, the amount of a compound or material may be expressed in terms of percent by weight ("wt %") of a given composition. As used herein the term wt % in reference to a named compound or material means the amount of the respective named compound or material, exclusive, for example, of any associated solvent, relative to a mixture or composition that contains the compound or material, expressed as a percent of the total weight of such mixture or composition. The term "active", as used herein in reference to a named compound, means the amount of the named compound, exclusive, for example, of any associated solvent.

In a first aspect, the polymer of the present invention comprises a chain of monomeric units. The polymer is a macromolecule having a relatively high molecular mass that comprises chains of multiple repetitions of the monomeric units, which are derived, actually or conceptually, from molecules of relatively low molecular mass and are connected to form a linear, branched, or network structure. The polymer typically has a linear or branched structure, more typically single strand linear or branched structure, but may optionally be crosslinked, In one embodiment, a polymer having a predominantly single strand linear or branched structure is lightly crosslinked, to form a polymer network having a low density of crosslinks. As used herein the term "single strand" in regard to a polymer means that monomeric units of the polymer are connected in such a way that adjacent monomeric units are joined to each other through two atoms, one on each of the adjacent monomeric units. The polymer may typically be regarded as having a "backbone", or main polymer chain, from which all branches and substituent groups of the polymer may be regarded as being pendant. Where two or more chains of the polymer could equally be considered to be the main chain of the polymer, that chain is selected as the main chain which leads to the simplest representation of the polymer molecule. The monomeric units of the polymer may be arranged in any sequence, including random, alternating, tapered, or block sequence, along the polymer chain.

In one embodiment, the polymer of the present invention comprises:
(a) one or more first monomeric units, each independently comprising at least one at least one bicycloheptyl-polyether or bicycloheptenyl-polyether group per monomeric unit, and
(b) one or more second monomeric units, each independently comprising at least one pendant linear or branched $(C_5-C_{50})$alkyl-polyether group per monomeric unit.

In one embodiment, the polymer of the present invention comprises:
(a) one or more first monomeric units, each independently comprising at least one branched $(C_5-C_{50})$alkyl-polyether group per monomeric unit, and
(b) one or more second monomeric units, each independently comprising at least one pendant linear $(C_5-C_{50})$alkyl-polyether group per monomeric unit.

In one embodiment, the first monomeric units each independently comprise, per monomeric unit, at least one branched $(C_5-C_{50})$alkyl-polyether group or bicycloheptyl-polyether or bicycloheptenyl-polyether group according to structure (I):

$$—R^{14}—R^{13}—R^{12}—R^{11} \tag{I}$$

wherein:
$R^{11}$ is branched $(C_5-C_{50})$alkyl or bicyclo[d.e.f]heptyl or bicyclo[d.e.f]heptenyl, wherein d is 2, 3, or 4, e is 1 or 2, f is 0 or 1, and the sum of d+e+f=5, and wherein the bicyclo[d.e.f]heptyl or bicyclo[d.e.f]heptenyl may, optionally, be substituted on one or more of the ring carbon atoms by one or more $(C_1-C_6)$alkyl groups,
$R^{12}$ is absent or is a bivalent linking group,
$R^{13}$ is bivalent polyether group, and
$R^{14}$ is absent or is a bivalent linking group.

Suitable bicycloheptyl- and bicycloheptenyl-moieties may be derived from, for example, terpenic compounds having core (non-substituted) 7 carbon atom bicyclic ring systems according to structures (II)-(V.b):

(II)

[2.2.1]

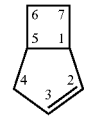

(III)

[3.2.0]

(IV.a)

[3.1.1]

-continued (IV.b)

[3.1.1]

(V.a)

[4.1.0]

(V.b)

[4.1.0]

In one embodiment, $R^{11}$ is bicyclo[d.e.f]heptyl or bicyclo[d.e.f]heptenyl wherein d is 2, 3, or 4, e is 1 or 2, f is 0 or 1, and the sum of d+e+f=5, and which may, optionally, be substituted on one or more of the ring carbon atoms by one or more $(C_1-C_6)$alkyl groups. More typically, $R^{11}$ is:

a bicyclo[2.2.1]heptyl or bicyclo[2.2.1]heptenyl group that is bonded to $R^2$, if present, or to $R^3$, if $R^2$ is not present, via its carbon atom at the 2-position or 3-position and is typically substituted on its carbon atom at the 7 position by one or two $(C_1-C_6)$alkyl radicals, more typically by two methyl radicals, or a bicyclo[3.1.1]heptyl or bicyclo[3.1.1]heptenyl group that is bonded to $R^2$, if present, or to $R^3$, if $R^2$ is not present, via its carbon atom at the 2-position or 3-position and is typically substituted on its carbon atom at the 6-position or 7-position by one or two $(C_1-C_6)$alkyl radicals, more typically by two methyl radicals.

In one embodiment, $R^{11}$ is selected from:

In one embodiment, $R^{11}$ is a branched $(C_5-C_{50})$ alkyl group, more typically a branched alkyl group according to structure (VI):

(VI)

—(CH$_2$)$_a$—$\overset{R^{15}}{\underset{H}{C}}$—R$^{16}$ wherein:
$R^{15}$ and $R^{16}$ are each independently $(C_1-C_{48})$alkyl, and
a is an integer of from 0 to 40,
provided that $R^{11}$, that is, $R^{15}$, $R^{16}$ and the —(CH$_2$)$_a$— radical taken together, comprises a total of from about 5 to about 50, more typically about 12 to about 50, carbon atoms.

More typically, $R^{12}$ is O, a bivalent hydrocarbon group, even more typically a methylene group or chain of from 2 to 6 methylene units, or a bivalent alkyleneoxyl group, such as ethyleneoxy. In one embodiment, $R^{12}$ is according to structure (VII):

—(CH$_2$)$_b$-A- (VII)

wherein A is O or absent, and b is an integer of from 1 to 6.

More typically, $R^{13}$ is a bivalent polyether group comprising a linear chain of from 2 to 100 units, each of which may independently be $(C_2-C_4)$oxyalkylene, more typically, $(C_2-C_3)$oxyalkylene. In one embodiment, $R^{13}$ is a bivalent polyether group comprising a chain of from 2 to 100 polymerized oxyethylene units and oxypropylene units, which may be arranged alternately, randomly, or in blocks. In one embodiment, $R^{13}$ is a bivalent polyether group comprising a block of polyoxyethylene units and a block of oxypropylene units, more typically, a block of polyoxyethylene units and a block of oxypropylene units, wherein the block of oxypropylene units is disposed between and links the block of oxyethylene units and the $R^{12}$ substituent, if present, or the $R^{11}$ substituent, if $R^{12}$ is not present.

In one embodiment, $R^{13}$ is according to structure (VIII):

$$-\!\!\left[(C_gH_{2g}O)_i-\!\!(C_hH_{2h}O)_j\right]_k\!\!-$$ (VIII)

wherein:
g and h are independently integers of from 2 to 5, more typically 2 or 3,
each i is independently an integer of from 1 to about 80, more typically from 1 to about 50,
each j is independently an integer of from 0 to about 80, more typically from 1 to about 50,
k is an integer of from 1 to about 50, provided that the product obtained by multiplying the integer k times the sum of i+j is from 2 to about 100.

If i≠0, j≠0, and g≠h, the respective —(C$_p$H$_{2p}$O)— and (—C$_q$H$_{2q}$O)— oxyalkylene units may be arranged randomly, in blocks, or in alternating order.

In one embodiment,
g=2,
h=3,
i is an integer of from 1 to 50, more typically 10 to 40, and even more typically from 15 to about 30,
j is an integer of from 1 to 30, more typically from 2 to 20, and even more typically from about 2 to about 10, and
k=1.

In one embodiment, $R^{14}$ is O, —(CH$_2$)$_n$—O—, or is according to structure (IX):

(IX)

$$-\!\!\overset{\overset{O}{\|}}{C}\!\!-\!\!A\!\!-$$

wherein:
n is an integer of from 1 to 6,
A is O or NR$^{17}$, and
$R^{17}$ is H or $(C_1-C_4)$alkyl.

The first monomeric units may be made by known synthetic techniques, such as, for example, by grafting of one or more groups according to structure (I) onto a polymer backbone, such as a hydrocarbon polymer backbone, a polyester polymer backbone, or a polysaccharide polymer backbone, or by copolymerization, with, for example, the second monomer and third monomer described below, of at least one first monomer selected from monomers that comprise a reactive functional group and at least one group according to structure (I) per molecule.

In one embodiment, the first monomeric units are derived from at least one first monomer selected from monomers that comprise a reactive functional group and at least one group according to structure (I) per molecule.

In one embodiment, the reactive functional group of the first monomer is an ethylenically unsaturated group and the first monomer selected from ethylenically unsaturated monomers that comprise at least one site of ethylenic unsaturation, more typically, an α-, β-unsaturated carbonyl moiety, and least one group according to structure (I) per molecule.

In one embodiment, the first monomer comprises one or more compounds according to structure (X):

(X)

wherein:
$R^{11}$, $R^{12}$, $R^{13}$, and $R^{14}$ are each as described above, and
$R^{18}$ is a moiety having a site of ethylenic unsaturation.

In one embodiment, the compound according to structure (X) is an α-, β-unsaturated carbonyl compound.

In one embodiment, $R^{18}$ is according to structure (XI):

(XI)

wherein $R^{19}$ is H or $(C_1-C_4)$alkyl.

In one embodiment, the one or more first monomers are selected from monomers according to structure (XII):

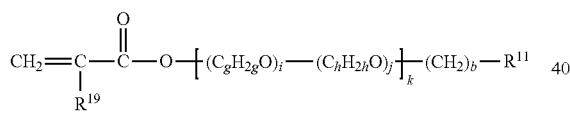

(XII)

wherein:
$R^{11}$ is bicyclo[d.e.f]heptyl or bicyclo[d.e.f]heptenyl wherein d is 2, 3, or 4, e is 1 or 2, f is 0 or 1, and the sum of d+e+f=5, and which may, optionally, be substituted on one or more of the ring carbon atoms by one or more $(C_1-C_6)$alkyl groups, and $R^{19}$, b, g, h, i, j, and k are each as defined above, more typically wherein $R_{19}$ is H or methyl, b is an integer of from 1 to 6, g=2, h=3, i is an integer of from 1 to 50, more typically 10 to 40, and even more typically from 15 to about 30, j is an integer of from 1 to 30, more typically from 2 to 20, and even more typically from about 2 to about 10, and k=1.

In one embodiment, the first monomer comprises one or more compounds according to structure (XIII):

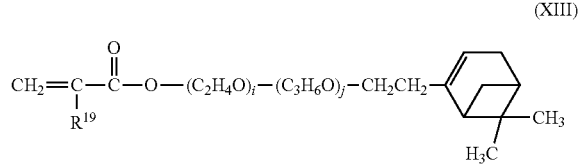

(XIII)

wherein i, j, and $R^{19}$ are each as described above, and, more typically, i is an integer of from 10 to 40, and even more typically from 15 to about 30, and still more typically form 20 to 30, and j is an integer of from 1 to 20, and even more typically from about 2 to about 10, and still more typically from 3 to 8.

In another embodiment, the first monomer comprises one or more compounds according to structure (XIV):

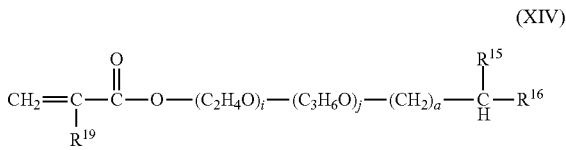

(XIV)

wherein a, i, j, and $R^{15}$, $R^{16}$, and $R^{19}$ are each as described above.

Suitable monomer may be made by known synthetic methods. For example, a bicycloheptenyl intermediate compound (XV), known as "Nopol":

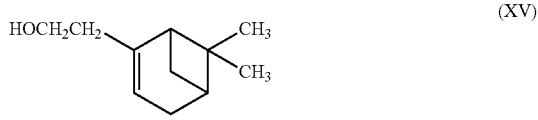

(XV)

is made by reacting β-pinene with formaldehyde, and
a bicycloheptyl intermediate compound (XVI), known as "Arbanol":

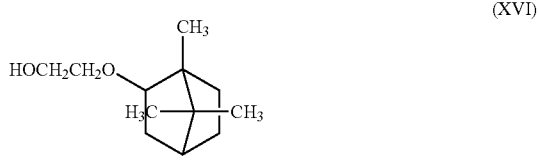

(XVI)

is made by isomerization of α-pinene to camphene and ethoxyhydroxylation of the camphene.

The bicycloheptyl- or bicycloheptenyl-intermediate may then be alkoxylated by reacting the bicycloheptyl- or bicycloheptenyl intermediate with one or more alkylene oxide compounds, such as ethylene oxide or propylene oxide, to form a bicycloheptyl-, or bicycloheptenyl-polyether intermediate. The alkoxylation may be conducted according to well known methods, typically at a temperature in the range of about 100° to about 250° C. and at a pressure in the range of from about 1 to about 4 bars, in the presence of a catalyst, such as a strong base, an aliphatic amine, or a Lewis acid, and an inert gas, such as nitrogen or argon.

The bicycloheptyl-, or bicycloheptenyl-polyether monomer may then be formed from the bicycloheptyl- or bicycloheptenyl-polyether intermediate by addition of a moiety containing an ethylenically unsaturated group to the bicycloheptyl- or bicycloheptenyl-polyether intermediate, by, for example, esterification, under suitable reaction conditions, of the bicycloheptyl- or bicycloheptenyl-polyether intermediate with, for example, methacrylic anhydride.

Alternatively, a monomer comprising a ethylenically unsaturated group, such as for example, a polyethylene glycol monomethacrylate, which may optionally be further alkoxylated, may be reacted with the bicycloheptyl- or bicycloheptenyl-intermediate to form the bicycloheptyl-, or bicycloheptenyl-polyether monomer.

In one embodiment, the second monomeric units each independently comprise, per monomeric unit, at least one group according to structure (XVII):

(XVII)

wherein:

$R^{21}$ is linear or branched $(C_5-C_{50})$alkyl, hydroxyalkyl, alkoxyalkyl, aryl, or aryalkyl, $R^{22}$ is a bivalent polyether group, $R^{23}$ is absent or is a bivalent linking group.

In one embodiment, $R^{21}$ is linear or branched $(C_5-C_{40})$alkyl, more typically linear or branched $(C_{10}-C_{40})$alkyl, even more typically, linear or branched $(C_{16}-C_{40})$alkyl, and still more typically linear or branched $(C_{16}-C_{30})$alkyl. In one embodiment, $R^{21}$ is tridecyl, tetradecyl, pentadecyl, hexadecyl, heptadecyl, octadecyl, nonadecyl, eicosyl, heneicosyl, behenyl, tricosyl, tetracosyl, pentacosyl, hexacosyl, heptacosyl, octacosyl, nonacosyl, triacontyl, dotriacontyl, tritriacontyl, tetratriacontyl, pentatriacontyl, hexatriacontyl, heptatriacontyl, octatriacontyl, nonatriacontyl, or tetracontyl, more typically, hexadecyl, heptadecyl, octadecyl, nonadecyl, eicosyl, or behenyl.

In embodiment $R^{21}$ is hydroxyalkyl, such as, for example, hydroxyhexadecyl, hydroxyoctadecyl, or hydroxyeicosyl, or alkoxyalkyl, such as for example, methoxyhexadecyl, methoxyoctadecyl, or methoxyeicosyl.

In embodiment $R^{21}$ is aryl, such as, for example, phenyl, methylphenyl, methoxyphenyl, dibutylphenyl, triisobutylphenyl, or tristyrylphenyl, or aralkyl, such as phenylmethyl, phenylethyl, or triphenylmethyl.

In one embodiment, the second monomeric units each independently comprise at least one group according to structure (XVII) above wherein $R^{21}$ is a linear $(C_5-C_{50})$alkyl group.

In one embodiment, the second monomeric units each independently comprise at least one group according to structure (XVII) above wherein $R^{21}$ is a branched $(C_5-C_{50})$alkyl group, more typically a branched $(C_5-C_{50})$alkyl group according to structure (VI) above.

In one embodiment, the second monomeric units comprise a mixture of second monomeric units that each independently comprise at least one group according to structure (XVII) above wherein $R^{21}$ is a linear $(C_5-C_{50})$alkyl group and second monomeric units that each independently comprise at least one group according to structure (XVII) above wherein $R^{21}$ is a branched $(C_5-C_{50})$alkyl group, more typically a branched $(C_5-C_{50})$alkyl group according to structure (VI) above.

In one embodiment, $R^{22}$ is a bivalent polyether group comprising a linear chain of from 2 to 100 units, each of which may independently be $(C_2-C_4)$oxyalkylene, more typically, $(C_2-C_3)$oxyalkylene. In one embodiment, $R^{22}$ is a bivalent polyether group comprising a chain of from 2 to 100 polymerized oxyethylene units.

In one embodiment, $R^{22}$ is according to structure (XVIII):

(XVIII)

wherein:

p and q are independently integers of from 2 to 5, more typically 2 or 3, each r is independently an integer of from 1 to about 80, more typically from 1 to about 50, each s is independently an integer of from 0 to about 80, more typically from 0 to about 50, t is an integer of from 1 to about 50, provided that the product obtained by multiplying the integer t times the sum of r+s is from 2 to about 100.

If $r \neq 0$, $s \neq 0$, and $p \neq q$, the respective —$(C_pH_{2p}O)$— and —$(C_qH_{2q}O)$— oxylakylene units may be arranged randomly, in blocks, or in alternating order.

In one embodiment, p=2, q=3, r is an integer of from 1 to 50, more typically 5 to 45, and even more typically from 10 to about 40, s is an integer of from 1 to 30, more typically from 2 to 20, and even more typically from about 2 to about 10, and t=1

In another embodiment, p=2, r is an integer of from 1 to 50, more typically 5 to 45, and even more typically from 10 to about 40, s is 0, and t=1.

In one embodiment, $R^{23}$ is O, —$(CH_2)_n$—O— wherein n is an integer of from 1 to 6, or is according to structure (IX) above, wherein A is O or $NR^{17}$, and $R^{17}$ is H or $(C_1-C_4)$alkyl.

The second monomeric units may be made by known synthetic techniques, such as, for example, by grafting of one or more groups according to structure (XVII) onto a polymer backbone, such as a hydrocarbon polymer backbone, a polyester polymer backbone, or a polysaccharide polymer backbone, or by copolymerization, with, for example, the above-described first monomer and the third monomer described below, of at least one second monomer selected from monomers that comprise a reactive functional group and at least one group according to structure (XVII) per molecule and that are copolymerizable with the first monomer.

In one embodiment, the second monomeric units are derived from at least one second monomer that comprises a reactive functional group and at least one group according to structure (XVII) per molecule and that are copolymerizable with the first monomer.

In one embodiment, the reactive group of the second monomer is an ethylenically unsaturated group and the second monomer is an ethylenically unsaturated monomer comprises at least one site of ethylenic unsaturation, more typically, an α-, β-unsaturated carbonyl moiety, and at least one group according to structure (XVII) per molecule and that are copolymerizable with the first monomer.

In one embodiment, the second monomer comprises one or more compounds according to structure (XIX):

(XIX)

wherein:

$R^{21}$, $R^{22}$, and $R^{23}$ are each as described above, and $R^{24}$ is a moiety having a site of ethylenic unsaturation.

In one embodiment, the compound according to structure (XIX) is an α-, β-unsaturated carbonyl compound. In one embodiment, $R^{23}$ is according to structure (XI) above.

In one embodiment, the second monomer comprises one or more compounds according to structure (XX):

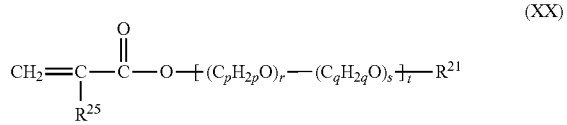

wherein $R^{21}$ is linear or branched $(C_5\text{-}C_{50})$alkyl, hydroxyalkyl, alkoxyalkyl, aryl, or aralkyl, $R^{25}$ is methyl or ethyl, and p, q, r, s, and t are each as described above.

In one embodiment, the second monomer comprises one or more compounds according to structure (XX) wherein $R^{21}$ is linear $(C_{16}\text{-}C_{22})$alkyl.

In one embodiment, the second monomer comprises one or more compounds according to structure (XX) wherein $R^{21}$ is a branched $(C_5\text{-}C_{50})$alkyl group, more typically a branched $(C_5\text{-}C_{50})$alkyl group according to structure (VI) above.

In one embodiment, the second monomer comprises one or more compounds according to structure (XX) wherein p=2, s=0, and t=1.

In one embodiment, the second monomer comprises one or more compounds according to structure (XX) wherein $R^{21}$ is linear $(C_{16}\text{-}C_{22})$alkyl, $R^{24}$ is methyl or ethyl, p=2, s=0, and t=1.

Suitable ethylenically unsaturated second monomers include:

alkyl-polyether (meth)acrylates that comprise at least one linear or branched $(C_5\text{-}C_{40})$alkyl-polyether group per molecule, such as hexyl polyalkoxylated (meth)acrylates, tridecyl polyalkoxylated (meth)acrylates, myristyl polyalkoxylated (meth)acrylates, cetyl polyalkoxylated (meth)acrylates, stearyl polyalkoxylated (methyl)acrylates, eicosyl polyalkoxylated (meth)acrylates, behenyl polyalkoxylated (meth)acrylates, melissyl polyalkoxylated (meth)acrylates, tristyrylphenoxyl polyalkoxylated (meth)acrylates, and mixtures thereof, alkyl-polyether (meth)acrylamides that comprise at least one $(C_5\text{-}C_{40})$alkyl-polyether substituent group per molecule, such as hexyl polyalkoxylated (meth)acrylamides, tridecyl polyalkoxylated (meth)acrylamides, myristyl polyalkoxylated (meth)acrylamides, cetyl polyalkoxylated (meth)acrylamides, stearyl polyalkoxylated (methyl)acrylamides, eicosyl polyalkoxylated (meth)acrylamides, behenyl polyalkoxylated (meth)acrylamides, melissyl polyalkoxylated (meth)acrylamides and mixtures thereof alkyl-polyether vinyl esters, alkyl-polyether vinyl ethers, or alkyl-polyether vinyl amides that comprise at least one $(C_5\text{-}C_{40})$alkyl-polyether substituent group per molecule such as vinyl stearate polyalkoxylate, myristyl polyalkoxylated vinyl ether, and mixtures thereof, as well as mixtures two or more of any of the above alkyl-polyether acrylates, alkyl-polyether methacrylates, alkyl-polyether acrylamides, alkyl-polyether methacrylamides, alkyl-polyether vinyl esters, alkyl-polyether vinyl ethers, and alkyl-polyether vinyl amides.

In one embodiment, the second monomer comprises one or more alkyl-polyalkoxylated (meth)acrylates that comprise one linear or branched $(C_5\text{-}C_{40})$alkyl-polyethoxylated group, more typically $(C_{10}\text{-}C_{22})$alkyl-polyethoxylated group per molecule, such as decyl-polyethoxylated (meth)acrylates, tridecyl-polyethoxylated (meth)acrylates, myristyl-polyethoxylated (meth)acrylates, cetyl-polyethoxylated (meth) acrylates, stearyl-polyethoxylated (methyl)acrylates, eicosyl-polyethoxylated (meth)acrylates, behenyl-polyethoxylated (meth)acrylates, even more typically decyl-polyethoxylated methacrylates, tridecyl-polyethoxylated methacrylates, myristyl-polyethoxylated methacrylates, cetyl-polyethoxylated methacrylates, stearyl-polyethoxylated methylacrylates, eicosyl-polyethoxylated methacrylates, behenyl-polyethoxylated methacrylates, and mixtures thereof.

In one embodiment, the polymer of the present invention further comprises third monomeric units, each independently comprising at least one acid group per monomeric unit.

In one embodiment, the third monomeric units each independently comprise, per monomeric unit, at least one group according to structure (XXI):

wherein $R^{31}$ is a moiety that comprises at least one carboxylic acid, sulfonic acid, or phosphoric acid group, and $R^{32}$ is absent or is a bivalent linking group.

In one embodiment, $R^{32}$ is O, $-(CH_2)_n-O-$, or is according to structure (IX) above, wherein n is an integer of from 1 to 6, A is O or $NR^{17}$, and $R^{17}$ is H or $(C_1\text{-}C_4)$alkyl.

In one embodiment, the third monomeric units each independently comprise one or two carboxy groups per monomeric unit and may, if the third monomeric unit comprises a single carboxy group, further comprise an ester group according to $-CH_2COOR^{33}$, wherein $R^{33}$ is alkyl, more typically, $(C_1\text{-}C_6)$alkyl.

The third monomeric units may be made by known synthetic techniques, such as, for example, by grafting of one or more groups according to structure (XXI) onto a polymer backbone, such as a hydrocarbon polymer backbone, a polyester polymer backbone, or a polysaccharide polymer backbone, or by polymerization, with, for example, the above described first and second monomers, of at least one third monomer selected from monomers that comprise a reactive functional group and at least one group according to structure (XXI) per molecule, and that are copolymerizable with the first and second monomers.

In one embodiment, the third monomeric units are derived from at least one third monomer that comprises a reactive functional group and at least group according to structure (XXI) per molecule and is copolymerizable with the first and second monomers.

In one embodiment, the reactive functional group of the third monomer is an ethylenically unsaturated group and the third monomer is an ethylenically unsaturated monomer that comprises at least one site of ethylenic unsaturation, more typically, an α-, β-unsaturated carbonyl moiety, and at least one group according to structure (XXI) per molecule and is copolymerizable with the first and second monomers.

In one embodiment the third monomer comprises one or more ethylenically unsaturated monocarboxylic acid monomers according to structure (XXII):

wherein:

$R^{31}$ and $R^{32}$ are each as described above, and $R^{34}$ is a moiety having a site of ethylenic unsaturation.

In one embodiment, the compound according to structure (XXII) is an α-, β-unsaturated carbonyl compound. In one embodiment, $R^{34}$ is according to structure (XI) above.

Suitable third monomers include, for example, ethylenically unsaturated carboxylic acid monomers, such as acrylic acid and methacrylic acid, ethylenically unsaturated dicarboxylic acid monomers, such ac maleic acid and fumaric acid, ethylenically unsaturated alkyl monoesters of dicarboxylic acid monomers, such as butyl methyl maleate, ethylenically unsaturated sulphonic acid monomers, such as vinyl sulfonic acid 2-acrylamido-2-methylpropane sulfonic acid, and styrene sulfonic acid, and ethylenically unsaturated phosphonic acid monomers, such as vinyl phosphonic acid and allyl phosphonic acid, salts of any thereof, and mixtures of any thereof. Alternatively, corresponding ethylenically unsaturated anhydride or acid chloride monomers, such as maleic anhydride, may be used and subsequently hydrolyzed to give a pendant moiety having two acid groups.

In one embodiment, the polymer of the present invention comprises third monomeric units derived from one or more third monomers selected from acrylic acid, methacrylic acid, and mixtures thereof.

In one embodiment, the polymer of the present invention further comprises one or more fourth monomeric units that differ from the first, second and third monomeric units.

In one embodiment, the fourth monomeric units each independently comprise, per monomeric unit, at least one group according to structure (XXIII):

(XXIII)

wherein:

$R^{41}$ is alkyl, hydroxyalkyl, alkoxyalkyl, cycloalkyl, aryl, aralkyl, or aryloxy, and $R^{42}$ is absent or is a bivalent linking group.

In one embodiment, $R^{41}$ is $(C_1-C_{22})$alkyl, $(C_1-C_{22})$hydroxyalkyl, $(C_2-C_{22})$alkoxyalkyl, $(C_6-C_{24})$cycloalkyl, $(C_6-C_{40})$aryl, or $(C_7-C_{40})$aralkyl, more typically $(C_2-C_{12})$alkyl.

In one embodiment, $R^{41}$ is $(C_1-C_{22})$alkyl, more typically, $(C_1-C_{12})$alkyl, even more typically $(C_1-C_6)$alkyl, and still more typically $(C_1-C_4)$alkyl.

In one embodiment, $R^{42}$ is O, $-(CH_2)_n-O-$, wherein n is an integer of from 1 to 6, or is according to structure (IX) above, wherein A is O or $NR^{17}$, and $R^{17}$ is H or $(C_1-C_4)$alkyl.

The fourth monomeric units may be made by known synthetic techniques, such as, for example, by grafting of one or more groups according to structure (XXIII) onto a polymer backbone, such as a hydrocarbon polymer backbone, a polyester polymer backbone, or a polysaccharide polymer backbone, or by polymerization, with, for example, of the above described first second, and third monomers, of at least one fourth monomer selected from monomers that comprise a reactive functional group and at least one group according to structure (XXIII) per molecule and that are copolymerizable with the first, second, and third monomers. Alternatively, the fourth monomeric units may simply be non-grafted portions of a polymer backbone, other portions of which have been grafted with groups according to structures (I), (XVII), and (XXI).

In one embodiment, the fourth monomeric units are derived from a fourth monomer that comprises a reactive functional group and a group according to structure (XXIII), and is copolymerizable with the first, second and third monomers.

In one embodiment, the reactive functional group of the fourth monomer is an ethylenically unsaturated group and the fourth monomer is an ethylenically unsaturated monomer comprising at least one site of ethylenic unsaturation, more typically, an α-, β-unsaturated carbonyl moiety and at least one group according to structure (XXIII) per molecule.

In one embodiment, the fourth monomer comprises one or more compounds according to structure (XXIV):

(XXIV)

wherein:

$R^{41}$ and $R^{42}$ are each as described above, and $R^{43}$ is a moiety having a site of ethylenic unsaturation.

In one embodiment, the compound according to structure (XXIV) is an α-, β-unsaturated carbonyl compound. In one embodiment, $R^{43}$ is according to structure (XI) above.

Suitable fourth monomers include unsaturated monomers at least one group according to structure (XXIII) per molecule, including (meth)acrylic esters such as: methyl(meth)acrylate, ethyl(meth)acrylate, butyl (meth)acrylate, isobutyl (meth)acrylate, cyclohexyl(meth)acrylate, 2-ethylhexyl (meth)acrylate, isodecyl(meth)acrylate, lauryl(meth)acrylate isobornyl (meth)acrylate, benzyl(meth)acrylate, hydroxyethyl(meth)acrylate, hydroxypropyl(meth)acrylate, methoxyethyl(meth)acrylate, ethoxyethyl (meth)acrylate, phenoxyethyl(meth)acrylate, tetrahydrofurfuryl(meth)acrylate, glycidyl(meth)acrylate, dimethylaminoethyl(meth)acrylate, diethylaminoethyl (meth)acrylate, tert-butylaminoethyl (meth)acrylate, and acetoxyethyl (meth)acrylate, (meth)acrylamides such as, (meth)acrylamide, N-methylol (meth)acrylamide, N-butoxyethyl(meth)acrylamide, N,N-dimethyl (meth)acrylamide, N-isopropyl(meth)acrylamide, N-tert-butyl (meth)acrylamide, N-tert-octyl(meth)acrylamide, and diacetone (meth)acrylamide, vinyl esters such as vinyl acetate, vinyl propionate, vinyl 2-ethylhexanoate, N-vinylamides such as: N-vinylpyrrolidinone, N-vinylcaprolactam, N-vinylformamide, and N-vinylacetamide, and vinyl ethers such as, methyl vinyl ether, ethyl vinyl ether, butyl vinyl ether, and hydroxybutyl vinyl ether, and ethylenically unsaturated aryl compounds, such as styrene.

In one embodiment, the polymer of the present invention comprises fourth monomeric units derived from one or more $(C_1-C_{22})$alkyl (meth)acrylic esters, more typically $(C_1-C_{12})$ alkyl(meth)acrylic esters, such as ethyl methacrylate, or ethylhexyl acrylate, more typically $(C_1-C_6)$alkyl (meth)acrylic esters, and even more typically $(C_1-C_4)$alkyl(meth)acrylic esters, such as ethyl acrylate or butyl acrylate.

In one embodiment, the polymer of the present invention is a crosslinked polymer that comprises crosslinks between the chains of polymerized monomers. Such crosslinks are typically derived from one or more crosslinker monomers by, for example, reacting a mixture of first, second, third, and fourth monomers in the presence of at least one crosslinking monomer. Suitable crosslinking monomers are compounds having more than one reactive functional group, such as for example, more than one site of unsaturation, typically ethylenic unsaturation, per molecule, that are copolymerizable with the reactive functional groups of the other monomers of mixture under the polymerization reaction conditions used. Suitable polyunsaturated crosslinkers are well known in the art. Monounsaturated compounds that further comprise a second reactive functional group that is capable of causing a formed copolymer to be crosslinked before, during, or after polymerization has taken place can also be utilized. Other useful crosslinking monomers include polyfunctional monomers containing multiple reactive groups, such as epoxide groups, isocyanate groups, and hydrolyzable silane groups. Various polyunsaturated compounds can be utilized to generate either a partially or substantially cross-linked three dimensional network. Suitable polyunsaturated crosslinker monomers include, for example, polyunsaturated aromatic monomers, such as divinylbenzene, divinyl naphthalene, and trivinylbenzene, polyunsaturated alicyclic monomers, such as 1,2,4-trivinylcyclohexane, di-functional esters of phthalic acid, such as diallyl phthalate, polyunsaturated aliphatic monomers, such as dienes, trienes, and tetraenes, including isoprene, butadiene, 1,5-hexadiene, 1,5,9-decatriene, 1,9-decadiene, 1,5-heptadiene, polyalkenyl ethers, such as triallyl pentaerythritol, diallyl pentaerythritol, diallyl sucrose, octaallyl sucrose, and trimethylolpropane diallyl ether, polyunsaturated esters of polyalcohols or polyacids, such as 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, poly(alkyleneoxy) glycol di(meth) acrylates, and polyethylene glycol di(meth)acrylate, alkylene bisacrylamides, such as methylenebisacrylamide and propylene bisacrylamide, hydroxy and carboxy derivatives of methylene bis-acrylamide, such as N,N'-bismethylol methylene bisacrylamide, polyalkyleneglycol di(meth)acrylates, such as ethyleneglycol di(meth)acrylate, diethyleneglycol di(meth)acrylate, and triethyleneglycol di(meth)acrylate, polyunsaturated silanes, such as dimethyldivinylsilane, methyltrivinylsilane, allyldimethylvinylsilane, diallydimethylsilane and tetravinylsilane, polyunsaturated stannanes, such as tetraallyl tin, diallyldimethyl tin. In one embodiment, the polymer of the present invention comprises crosslinks derived from one or more crosslinker monomers having more than one (meth)acrylic group per molecule, such as, for example, allyl methacrylate, ethylene glycol dimethacrylate, butylene glycol dimethacrylate, diallyl pentaerythritol, methylenebisacrylamide, pentaerythritol di-, tri- and tetra-acrylates, divinyl benzene, poly(alkyleneoxy)glycol di(meth) acrylates, such as polyethylene glycol diacrylates, bisphenol A diacrylates, butanediol dimethacrylate, 2,2-dimethylpropanediol dimethacrylate, ethylene glycol dimethacrylate, phenylene diacrylate, or a mixture thereof.

In one embodiment, the polymer of the present invention comprises:
(a) one or more first monomeric units,
(b) one or more second monomeric units,
(c) one or more third monomeric units, and
(d) one or more fourth monomeric units,
each as described above.

In one embodiment of the polymer of the present invention:
(a) the first monomeric units each independently comprise at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may, optionally, be substituted on one or more ring carbon atoms by one or two ($C_1$-$C_6$)alkyl groups per carbon atom,
(b) the second monomeric units each independently comprise at least one pendant linear or branched ($C_5$-$C_{50}$)alkyl-polyether group per monomeric unit, provided that the first and second monomeric units cannot both comprise a branched ($C_5$-$C_{50}$)alkyl-polyether group,
(c) the third monomeric units each independently comprise at least one carboxylic acid, sulfonic acid, or phosphoric acid group per molecule, and
(d) the fourth monomeric units each independently comprise at least one alkyl, hydroxyalkyl, alkoxyalkyl, cycloalkyl, aryl, aralkyl, or aryloxy group per monomeric unit.

In one embodiment:
(a) the first monomeric units each independently comprise at least one bicycloheptyl-polyether or bicycloheptenyl-polyether group, which may, optionally, be substituted on one or more ring carbon atoms by one or two ($C_1$-$C_6$)alkyl groups per carbon atom, per monomeric unit,
(b) the second monomeric units, each independently comprise at least one pendant linear or branched ($C_5$-$C_{50}$)alkyl-polyether group per monomeric unit,
(c) the third monomeric units each independently comprise at least one carboxylic acid, sulfonic acid, or phosphoric acid, more typically carboxylic acid, group per molecule, and
(d) the fourth monomeric units each independently comprise at least one alkyl, more typically ($C_1$-$C_{22}$)alkyl, group per monomeric unit.

In one embodiment, the polymer of the present invention comprises, based on 100 monomeric units,
(a) from about 0.01, more typically from about 0.05, and even more typically from about 0.10 of the first monomeric units, to about 10, more typically to about 5, and even more typically to about 2, of the first monomeric units,
(b) from about 0.01, more typically from about 0.05, and even more typically from about 0.10 of the second monomeric units, to about 10, more typically to about 5, and even more typically to about 2, of the second monomeric units, and
(c) from about 25, more typically from about 30, and even more typically from about 35 of the third monomeric units, to about 70, more typically to about 65, and even more typically to about 60, of the third monomeric units,
(d) from about 30, more typically from about 40, and even more typically from about 45 of the fourth monomeric units, to about 75, more typically to about 70, and even more typically to about 65 of the fourth monomeric units.

In one embodiment, the polymer of the present invention comprises, based on 100 pbw of the polymer,
(a) from about 0.1, more typically from about 0.5, and even more typically from about 1.0 pbw of the first monomeric units, to about 20, more typically to about 15, and even more typically to about 10, pbw of the first monomeric units,
(b) from about 0.1, more typically from about 0.5, and even more typically from about 1.0, pbw of the second monomeric units, to about 20, more typically to about 15, and even more typically to about 10, pbw of the second monomeric units, and
(c) from about 20, more typically from about 25, and even more typically from about 30, pbw of the third monomeric units, to about 60, more typically to about 55, and even more typically to about 60, pbw of the third monomeric units, and
(d) from about 25, more typically from about 35, and even more typically from about 40, pbw of the fourth monomeric units, to about 70, more typically to about 65, and even more typically to about 60, pbw of the fourth monomeric units.

In one embodiment, the polymer of the present invention comprises from about 0.4 to about 5, more typically from about 0.6 to about 4, and even more typically from about 0.8 to about 2 of the first monomeric units per each of the second monomeric units.

In one embodiment, the polymer of the present invention comprises from 0.4, more typically from 0.6, and even more typically from 0.8 to less than 1 of the first monomeric units per each of the second monomeric units. In one embodiment, the polymer of the present invention comprises from 0.4 to less than 1, more typically from about 0.6 to less than 1, and even more typically from about to 0.8 to less than 1 of the first monomeric units per each of the second monomeric units.

In one embodiment, the polymer of the present invention comprises from 1, more typically from about 1.05 and even more typically 1.1, to 2.5 more typically to 2, and even more typically 1.8, of the first monomeric units per each of the second monomeric units. In one embodiment, the polymer of the present invention comprises from 1 to 2.5, more typically from about 1.05 to 2, and even more typically from about 1.1 to 1.8 of the first monomeric units per each of the second monomeric units.

In one embodiment, the polymer is the product of copolymerization of a mixture of monomers, comprising:
(a) one or more first monomers,
(b) one or more second monomers,
(c) one or more third monomers, and
(d) one or more fourth monomers,
each as described above.

In one embodiment:
(a) the one or more first monomers are each independently selected from monomers that comprise a reactive functional group and at least one bicycloheptyl-polyether, bicycloheptenyl-polyether, or branched ($C_5$-$C_{50}$)alkyl-polyether group per molecule, wherein the bicycloheptyl-polyether or bicycloheptenyl-polyether group may optionally be substituted on one or more ring carbon atoms by one or two ($C_1$-$C_6$)alkyl groups per carbon atom,
(b) the one or more second monomers are each independently selected from monomers that comprise a reactive functional group and at least one pendant straight or branched ($C_5$-$C_{50}$)alkyl-polyether group per molecule and that are copolymerizable with the first monomer, provided that the first and second monomer cannot both comprise a branched ($C_5$-$C_{50}$)alkyl-polyether group,
(c) the one or more third monomers are each independently selected from monomers that comprise a reactive functional group and at least one carboxylic acid, sulfonic acid, or phosphoric acid group per molecule and that are copolymerizable with the first and second monomers, and
(d) the one or more fourth monomers are each independently selected from monomers that comprise a reactive functional group and at least one alkyl, hydroxyalkyl, alkoxyalkyl, cycloalkyl, aryl, aralkyl, or aryloxy group per monomeric unit and that are copolymerizable with the first, second and third monomers.

In one embodiment:
(a) the one or more first monomers are each independently selected from monomers that comprise a reactive functional group, more typically an ethylenically unsaturated group, and at least one bicycloheptyl-polyether or bicycloheptenyl-polyether group, which may optionally be substituted on one or more ring carbon atoms by one or two ($C_1$-$C_6$)alkyl groups per carbon atom per molecule, per molecule,
(b) the one or more second monomers are each independently selected from monomers that comprise a reactive functional group, more typically an ethylenically unsaturated group, and at least one pendant straight or branched ($C_5$-$C_{50}$)alkyl-polyether group per molecule and that are copolymerizable with the first monomer,
(c) the one or more third monomers are each independently selected from monomers that comprise a reactive functional group, more typically an ethylenically unsaturated group, and at least one carboxylic acid, sulfonic acid, or phosphoric acid, more typically, carboxylic acid, group per molecule and that are that are copolymerizable with the first and second monomers, and
(d) the one or more fourth monomers are each independently selected from monomers that comprise a reactive functional group, more typically an ethylenically unsaturated group, and at least one alkyl, more typically ($C_1$-$C_{22}$)alkyl, group per molecule unit and that are copolymerizable with the first, second and third monomers.

In one embodiment, the polymer of the present invention is the product of polymerization of a mixture of monomers comprising, based on the molar amount of the monomers:
(a) from about 0.01 mole %, more typically from about 0.05 mole %, and even more typically from about 0.10 mole % of the one or more first monomers, to about 10 mole %, more typically to about 5 mole %, and even more typically to about 2 mole % of the one or more first monomers,
(b) from about 0.01 mole %, more typically from about 0.05%, and even more typically from about 0.10 mole %, to about 10 mole %, more typically to about 5 mole %, and even more typically to about 2 mole %, of the one or more second monomers,
(c) from about 25 mole %, more typically from about 30 mole %, and even more typically from about 35 mole % of the third monomers to about 70 mole %, more typically to about 65 mole % and even more typically to about 60 mole % of the one or more third monomers, and
(d) from about 30, more typically from about 40, and even more typically from about 45, pbw of the fourth monomers, to about 75, more typically to about 70, and even more typically to about 65, pbw of the one or more fourth monomers.

In one embodiment, the polymer of the present invention is the product of polymerization of a mixture of monomers comprising, based on the 100 pbw of the total amount of the monomers:
(a) from about 0.1, more typically from about 0.5, and even more typically from about 1.0 pbw of the first monomers, to about 20, more typically to about 15, and even more typically to about 10, pbw of the one or more first monomers,
(b) from about 0.1, more typically from about 0.5, and even more typically from about 1.0, pbw of the second monomers, to about 20, more typically to about 15, and even more typically to about 10, pbw of the one or more second monomers, and
(c) from about 20, more typically from about 25, and even more typically from about 30, pbw of the third monomers, to about 60, more typically to about 55, and even more typically to about 50, pbw of the one or more third monomers, and
(d) from about 25, more typically from about 35, and even more typically from about 40, pbw of the third monomers, to about 70, more typically to about 65, and even more typically to about 60, pbw of the one or more fourth monomers.

In one embodiment, the polymer comprises the product of polymerization of a mixture of monomers comprising, based on the molar amount of monomers, from about 0.4 to about 5, more typically, from about 0.6 to about 4, and even more typically from about 0.8 to about 2 moles of the one or more first monomers per each mole of the one or more second monomers.

In one embodiment, the polymer of the present invention comprises from 0.4, more typically from 0.6, and even more typically from 0.8 mole to less than 1 mole of the one or more first monomers per each mole of the one or more second monomers. In one embodiment, the polymer of the present invention comprises from 0.4 to less than 1 mole, more typically from about 0.6 to less than 1 mole, and even more typically from about to 0.8 to less than 1 mole of the one or more first monomers per each mole of the one or more second monomers.

In one embodiment, the polymer of the present invention comprises from 1, more typically from about 1.05 and even more typically 1.1 moles, to 2.5 more typically to 2, and even more typically 1.8, moles of the one or more first monomer per each mole of the one or more second monomers. In one embodiment, the polymer of the present invention comprises from 1 to 2.5 moles, more typically from about 1.05 to 2 moles, and even more typically from about 1.1 to 1.8 moles of the one or more first monomers per each mole of the one or more second monomers.

The polymer of the present invention can be conveniently prepared from the above-described monomers by known aqueous emulsion polymerization techniques using free-radical producing initiators, typically in an amount from 0.01 percent to 3 percent, based on the weight of the monomers.

In one embodiment, the polymerization is conducted at a pH of about 5.0 or less. Polymerization at an acid pH of about 5.0 or less permits direct preparation of an aqueous colloidal dispersion having relatively high solids content without the problem of excessive viscosity.

In one embodiment, the polymerization is conducted in the presence of one or more free-radical producing initiators selected from peroxygen compounds. Useful peroxygen compounds include inorganic persulfate compounds such as ammonium persulfate, potassium persulfate, sodium persulfate, peroxides such as hydrogen peroxide, organic hydroperoxides, for example, cumene hydroperoxide, and t-butyl hydroperoxide, organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite), and other free-radical producing materials or techniques such as 2,2'-azobisisobutyronitrile and high energy radiation sources.

In one embodiment, the polymerization is conducted in the presence of one or more emulsifiers. Useful emulsifiers include anionic surfactants, nonionic surfactants, amphoteric surfactants, and zwitterionic surfactants. In one embodiment, the emulsion polymerization is conducted in the presence of one or more anionic surfactants. Examples of anionic emulsifiers are the alkali metal alkyl aryl sulfonates, the alkali metal alkyl sulfates and the sulfonated alkyl esters. Specific examples of these well-known emulsifiers are sodium dodecyl benzene sulfonate, sodium dodecyl butylnaphthalene sulfonate, sodium lauryl sulfate, ammonium lauryl sulfate, ammonium laureth sulfate, disodium dodecyl diphenyl ether disulfonate, disodium n-octadecyl sulfosuccinamate and sodium dioctyl sulfosuccinate. Known nonionic emulsifiers include, for example, fatty alcohols, alkoxylated fatty alcohols, and alkylpolyglucosides.

The emulsion polymerization may, optionally, be conducted in the presence, in an amount up to about 10 parts per 100 parts of polymerizable monomers, of one or more chain transfer agents. Representative chain transfer agents are carbon tetrachloride, bromoform, bromotrichloromethane, and long-chain alkyl mercaptans and thioesters, such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate.

Optionally, other ingredients well known in the emulsion polymerization art may be included, such as chelating agents, buffering agents, inorganic salts and pH adjusting agents.

In one embodiment, the polymerization is carried out at a temperature of from about 20° C. to 100° C., more typically from about 50° C. to about 90° C. or between about 60° C. and about 90° C., and even more typically from about 60° C. to about 80° C., but higher or lower temperatures may be used. The polymerization can be conducted batchwise, stepwise, or continuously with batch and/or continuous addition of the monomers, in a conventional manner.

The monomers can be copolymerized in such proportions, and the resulting polymers can be physically blended, to give products with the desired balance of properties for specific applications. For example, for analogous polymers of a given molecular weight, increasing the amount of first monomer tends to increase the yield strength exhibited by the polymer, increasing the relative amount of second monomer tends to increase the viscosity of the polymer. The properties of the polymer may be adjusted by selection of the third and fourth monomers and their relative amounts. For example, the addition of styrene as a fourth monomer tends to increase to a higher pH the adjustment required to dissolve the emulsion in an aqueous coating composition.

The polymeric products according to the present invention prepared by emulsion polymerization at an acid pH are in the form of stable aqueous colloidal dispersions containing the polymer dispersed as discrete particles having average particle diameters of about 400 to about 3000 Å and preferably about 600 to about 1750 Å, as measured by light scattering. Dispersions containing polymer particles smaller than about 400 Å are difficult to stabilize, while particles larger than about 3000 Å reduce the ease of dispersion in the aqueous products to be thickened.

In one embodiment, the polymer composition of the present invention is in the form of an aqueous polymer dispersion, typically having a solids content including the polymer and any surfactants that may be present and based on the total weight of the polymer dispersion, of up to about 60 wt % and, more typically about 20 to about 50 wt %.

Alternatively, polymers according to the present invention can be made using known solution polymerization techniques, wherein the reactant monomers and initiator are dissolved in an appropriate solvent such as toluene, xylene, tetrahydrofuran, or mixtures thereof. Polymerization can be accomplished within the time necessary at a given reaction temperature, e.g., from about 60° C. to about 80° C. for from about 2 to about 24 hours. The polymer product can be isolated through normal separation techniques, including solvent stripping.

In one embodiment, the polymer of the present invention exhibits a weight average molecular weight, as determined by gel permeation chromatography and light scattering of a solution of the polymer in tetrahydrofuran and compared to a polystyrene standard, of greater than or equal to 30,000 grams per mole ("g/mole"). In one embodiment, the polymer of the present invention exhibits a weight average molecular weight of from 30,000 g/mole, more typically from about 100,000 g/mole, and even more typically from about 150,000 g/mole, to about 1,500,000 g/mole, more typically to about 1,000,000 g/mole, and even more typically to about 800,000 g/mole.

In one embodiment, the polymer composition of the present invention is in the form of an aqueous colloidal polymer dispersion. When the polymer composition is in the form of an aqueous colloidal polymer dispersion, the composition is maintained at a pH of about 5 or less to maintain stability. More typically, the aqueous colloidal polymer dispersion composition has a pH of about 2 to about 3. When thickening of the composition is desired, the pH of the composition can be increased to a value above about 5 by addition of a base to solubilize the polymer.

The polymers and polymer compositions according to the present invention are pH-responsive. At the lower pH levels at which the emulsion polymerization takes place, for example, at pH levels of 5 or less, the composition is typically relatively thin or non-viscous. When the pH of the polymer dispersion is neutralized or adjusted by addition of a base to a pH of about 5 or more, more typically about 5.5 or more, even more about 6 to about 12, the composition thickens substantially. The composition turns from semi-opaque or opaque to translucent or transparent as viscosity increases. Viscosity increases as polymer dissolves partially or completely in the aqueous phase of the composition. Neutralization can occur in situ when the emulsion polymer is blended with the base and added to the aqueous phase. Or, if desired for a given application, neutralization can be carried out when blending with an aqueous product. Useful bases include, but are not limited to, ammonia, an amine, sodium hydroxide, potassium carbonate or the like.

The polymer of the present invention is particularly useful as a thickener for a wide variety of liquid medium-based compositions, typically water-based compositions. Such compositions include brine, slurries, and colloidal dispersions of water-insoluble inorganic and organic materials, such as natural rubber, synthetic or artificial latexes. As used herein, "liquid medium" means a medium that is in the liquid phase at a temperature of 25° C. and a pressure of one atmosphere. The liquid medium may be a non-aqueous polar protic organic liquid medium, such as, methanol, ethanol, propanol, glycerol, ethylene glycol, propylene glycol, diethylene glycol, poly(ethylene glycol)s, ethylene glycol monobutyl ether, dipropylene glycol methyl ether, and ethylene glycol phenyl ether, or an aqueous liquid medium. In one embodiment, the liquid medium is an aqueous liquid medium. As used herein, the terminology "aqueous medium" means a single phase liquid medium that contains more than a trace amount of water, typically, based on 100 pbw of the aqueous medium, more than 0.1 pbw water. Suitable aqueous media more typically comprise, based on 100 pbw of the aqueous medium, greater than about 5 pbw water, even more typically greater than 10 pbw water. In one embodiment, the aqueous liquid medium comprises, based on 100 pbw of the aqueous medium, greater than 40 pbw water, more typically, greater than 50 pbw water. The aqueous medium may, optionally, further comprise water soluble or water miscible components dissolved in the aqueous medium. The terminology "water miscible" as used herein means miscible in all proportions with water. Suitable water miscible organic liquids include, for example, $(C_1-C_6)$alcohols, such as methanol, ethanol, propanol, and $(C_1-C_6)$polyols, such as glycerol, ethylene glycol, propylene glycol, and diethylene glycol, The composition of the present invention may, optionally, further comprise one or more water insoluble or water immiscible components, such as a water immiscible organic liquid, such as, for example, a vegetable oil or alkylated vegetable oil, wherein the combined aqueous medium and water insoluble or water immiscible components form a micro emulsion, or a multiphase system such as, for example, an emulsion, a suspension or a suspoemulsion, in which the aqueous medium is in the form of a discontinuous phase dispersed in a continuous phase of the water insoluble or water immiscible component, or, more typically, the water insoluble or water immiscible component is in the form of a discontinuous phase dispersed in a continuous phase of the aqueous medium. The polymer of the present invention is especially useful in areas requiring thickening of aqueous compositions at neutral pHs, such as in personal care compositions. The polymer of the present invention may be used to thicken a polar protic organic liquid, such as an alcohol, typically $(C_2-C_4)$alcohol, based compositions, such as, for example to thicken an ethanol based liquid composition to form an antibacterial gel composition.

In one embodiment, the aqueous composition comprising the polymer of the present invention exhibits viscoelastic properties over a wide range of pH, for example at a pH of greater than or equal to 3, more typically greater than or equal to 4. Most applications for the polymer are at neutral to alkaline pH values, typically at pH values greater than or equal to about 5, more typically greater than or equal to about 5.5, even more typically of from about 6 to about 12, still more typically from about 6 to about 9.

In one embodiment, an aqueous composition comprising the polymer of the present invention exhibits non-Newtonian "shear thinning" viscosity, that is, a viscosity that, within a given range of shear stress, decreases with increasing shear stress.

In one embodiment, an aqueous composition comprising the polymer of the present invention exhibits a "yield strength", that is, a minimum shear stress required to initiate flow of the composition, and exhibits shear thinning behavior over some range of shear stress above the yield strength, such as for example, a yield strength of greater than 0 Pa, more typically of from about 0.1 Pa and even more typically from about 1 Pa, to about 10 Pa, more typically to about 6 Pa, and even more typically to about 2 Pa, even in the non-crosslinked embodiments of the polymer. In one embodiment, the polymer of the present invention is not cross-linked and provides a yield strength of greater than 0 Pa, more typically greater than 0.1 Pa and even more typically greater than 1 Pa.

The polymer of the present invention may be used in combination with other thickeners, such as natural gums, resins, polysaccharides, and synthetic polymeric thickeners The polymer of the present invention may be added to liquid compositions within a wide range of amounts, typically from greater than 0 to about 50 pbw of the polymer, more typically from greater than 0 to about 20 pbw of the polymer, per 100 pbw of the composition, depending on the desired system properties and end use applications. The polymer may typically be added at any stage or at multiple stages of the preparation of composition, such as, by addition to water before addition of other ingredients, by addition to the composition among other added ingredients, or by addition after addition of any other ingredients, as the final ingredient in a series of additions and/or as a post-addition to the composition, such as, for example, as a post-addition to adjust the rheological properties of the composition.

In one embodiment, the present invention is directed to an aqueous coating composition comprising water, the polymer of the present invention, and a latex polymer. The latex polymers are typically film-forming at temperatures about 25° C. or less, either inherently or through the use of plasticizers. Such coating compositions include water-based consumer and industrial paints, sizing, adhesives and other coatings for paper, paperboard, textiles, and the like.

A latex coating according to the present invention may optionally further comprise various adjuvants known in the art, such as pigments, fillers and extenders. Useful pigments include, but are not limited to, titanium dioxide, mica, and iron oxides. Useful fillers and extenders include, but are not limited to, barium sulfate, calcium carbonate, clays, talc, and silica. The compositions of the present invention described herein are compatible with most latex paint systems and provide highly effective and efficient thickening.

In one embodiment, a latex coating composition according to the present invention comprises from about 0.05 to about 5.0 weight percent, more typically about 0.1 to about 3.0 weight percent, of the polymer of the present invention, based on total weight of the latex coating composition, including all of its components, such as water, polymer of the present invention, latex polymer, pigment, and any adjuvants.

In formulating latexes and latex paints and coatings, physical properties that may be considered include, but are not limited to, viscosity versus shear rate, ease of application to surface, spreadability, and shear thinning.

The polymer of the present invention of the present invention is suitable in the preparation of compositions and products for personal care, health care, household care and industrial and institutional care.

In one embodiment, the present invention is directed to a personal or topical health care composition that comprises a polymer of the present invention. Suitable personal care compositions, such as cosmetics, toiletries, health and beauty aids, cosmeceuticals) and topical health care compositions include without limitation, hair care products, such as shampoos (including combination shampoos, such as "two-in-one" conditioning shampoos), hair conditioners, post-shampoo rinses, hair colorants, setting, styling, and style maintenance agents including setting aids, such as gels and sprays, grooming aids, such as pomades, conditioners, perms, relaxers, hair smoothing products, and the like, skin care products (facial, body, hands, scalp and feet), such as creams, lotions, conditioners, and cleansing products, such as facial washes and body washes, anti-acne products, anti-aging products (exfoliant, keratolytic, anticellulite, antiwrinkle, and the like), skin protectants such as sunscreens, sunblock, barrier creams, oils, silicones, and the like, skin color products (whiteners, lighteners, sunless tanning accelerators, and the like), hair colorants (hair dyes, hair color rinses, highlighters, bleaches and the like), pigmented skin colorants (face and body makeups, foundation creams, mascara, rouge, lip products, and the like), bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softeners, and the like), oral care products, such as toothpastes and mouthcare products, and any aqueous acidic to basic composition to which an effective amount of the polymer of the present invention can be incorporated for achieving a beneficial or desirable, physical or chemical, effect therein during storage and/or usage. Compositions for personal care and topical health care can be in the form of, without being limited thereto, liquids, such as rinses, gels, sprays, emulsions, such as lotions and creams, shampoos, pomades, foams, ointments, tablets, sticks, such as lip care products, makeup, and suppositories, and like products, which are applied to skin and hair and remain in contact therewith until removed as by rinsing with water or washing with shampoo or soap. Gels can be soft, stiff, or squeezable. Emulsions can be oil-in-water, water-in-oil, or multiphase. Sprays can be non-pressurized aerosols delivered from manually pumped finger-actuated sprayers or can be pressurized aerosols. The polymer of the present invention can be formulated in an aerosol composition, such as in a spray, mousse, or foam forming formulation, where a chemical or gaseous propellant is required. Physiologically and environmentally tolerable propellants, such as compressed gases, fluorinated hydrocarbons and liquid volatile hydrocarbons, and the amounts and suitable combinations to be used, are well known in the cosmetic and pharmaceutical art and literature.

In one embodiment, the present invention is directed to a personal care composition comprising a liquid medium, typically an aqueous medium, and more typically water, one or more surfactants, and the polymer of the present invention.

In one embodiment, the personal care composition comprises, based on 100 parts by weight ("pbw") of the personal care composition, from about 10 to about 80 pbw, more typically from about 20 to about 70 pbw, of a liquid medium, typically an aqueous medium, and more typically water, from about 1 to about 50 pbw of one or more surfactants, and from greater than 0 to about 20 pbw, more typically from about 0.05 to about 10 pbw, and still more typically from about 0.1 to about 5 pbw, of the polymer of the present invention.

Suitable surfactants include anionic surfactants, cationic surfactants, amphoteric surfactants, zwitterionic surfactants, nonionic surfactants, and mixtures thereof.

Anionic surfactants are generally known and include, for example, alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, alkyl sulfosuccinates, alkyl alkoxy sulfosuccinates, dialkyl phosphates, alkyl lactylates, glutamate surfactants, isethionate surfactants, taurate surfactants, sarcosinate surfactants, and salts thereof, as well as mixtures of such compounds, wherein the cationic counterion of an anionic surfactant in salt form is typically selected from sodium, potassium, lithium, calcium, magnesium, ammonium, $(C_1-C_6)$alkyl ammonium cations. Specific examples of suitable anionic surfactant include ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium trideceth sulfate, sodium tridecyl sulfate, ammonium trideceth sulfate, ammonium tridecyl sulfate, disodium laureth sulfosuccinate, sodium monoalkyl phosphate, sodium dialkyl phosphate, ammonium cocoyl sulfate, sodium cocoyl sulfate, potassium cocoyl sulfate, monoethanolamine cocoyl sulfate, sodium tridecyl benzene sulfonate, and sodium dodecyl benzene sulfonate, sodium lauroyl isethionate, potassium methyl myristyl taurate, ammonium oleoyl sarcosinate and mixture thereof.

Cationic surfactants are generally known and include for example, mono-cationic surfactants according to formula (XXV):

wherein:
$R^{51}$, $R^{52}$, $R^{53}$, and $R^{54}$ are each independently H or an organic group, provided that at least one of $R^{51}$, $R^{52}$, $R^{53}$, and $R^{54}$ is not hydrogen, and $X^-$ is an anion, more, chloride, bromide, methosulfate, ethosulfate, lactate, saccharinate, acetate or phosphate anion.

As referred to herein, the term "cationic surfactants" does not include cationic polymers.

If one to three of $R^{51}$, $R^{52}$, $R^{53}$, and $R^{54}$ of the compound of structure (XXV) are each H, then the compound according to structure (XXV) is an amine salt. Suitable amine slat type cationic surfactants include polyethoxylated (2) oleyl/stearyl amine, ethoxylated tallow amine, cocoalkylamine, oleylamine, and tallow alkyl amine.

If $R^{51}$, $R^{52}$, $R^{53}$, and $R^{54}$ of the compound of structure XXV are each independently an organic group, then the compound of structure XXV is a quaternary ammonium compound. In one embodiment, $R^{51}$, $R^{52}$, $R^{53}$, and $R^{54}$ are each independent $(C_8-C_{24})$ branched or linear hydrocarbon groups which may comprise additional functionality such as, for example, fatty acids or derivatives thereof, including esters of fatty acids and fatty acids with alkoxylated groups, alkyl amido groups, aromatic rings, heterocyclic rings, phosphate groups, epoxy groups, and hydroxyl groups. The nitrogen atom may also be part of a heterocyclic or aromatic ring system, e.g., cataphyll morpholinium ethosulfate or steapyrium chloride. Specific examples of suitable quaternary ammonium compounds include cetyl trimethyl ammonium bromide, cetyl trimethyl ammonium chloride, myristyl trimethyl ammonium bromide, stearyl dimethyl benzyl ammonium chloride, oleyl dimethyl benzyl ammonium chloride, lauryl/myristryl trimethyl ammonium methosulfate, cetyl dimethyl (2)hydroxyethyl ammonium dihydrogen phosphate), cocotrimonium chloride, distearyldimonium chloride, stearyl octyldimonium methosulfate, isostearaminopropalkonium chloride, dihydroxypropyl PEG-5 linoleaminium chloride, PEG-2 stearmonium chloride, Quaternium 18, Quaternium 32, Quaternium 80, Quaternium 82, Quaternium 84, behentrimonium chloride, dicetyl dimonium chloride, behentrimonium methosulfate, tallow trimonium chloride, behenamidopropyl ethyl dimonium ethosulfate, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, isostearyl benzylimidonium chloride, cocoyl benzyl hydroxyethyl imidazolinium chloride, cocoyl hydroxyethylimidazolinium PG-chloride phosphate, stearyl hydroxyethylimidonium chloride, and mixtures thereof.

Amphoteric surfactants are generally known. As referred to herein, the term "amphoteric surfactants" does not include amphoteric polymers. Suitable amphoteric surfactants include the alkali metal, alkaline earth metal, ammonium or substituted ammonium salts of alkyl amphodipropionates, alkyl amphoacetates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropylsulfonate, caproamphodiacetate, caproamphoacetate, caproamphodipropionate, and stearoamphoacetate, cocoamidopropyl hydroxysultaine, and mixtures thereof. Specific examples of suitable amphoteric surfactant include sodium lauroamphoacetate, sodium lauroamphopropionate, disodium lauroamphodiacetate, sodium cocoamphoacetate, disodium cocoamphodiacetate, and mixtures thereof.

Zwitterionic surfactants are generally known and include betaine surfactants and sultaine surfactants, such as for example decyl dimethyl betaine, undecyl dimethyl betaine, dodecyl dimethyl betaine, tridecyl dimethyl betaine, tetradecyl dimethyl betaine, coco dimethyl betaine, hexadecyl dimethyl betaine, heptadecyl dimethyl betaine, octadecyl dimethyl betaine, dodecylamidopropyl dimethyl betaine, cocoamidopropyl betaine cocoamidopropyl dimethyl betaine, oleylamidopropyl betaine, lauryl dihydroxypropyl glycinate, lauryl di(hydroxy-poly(ethoxy)) glycinate, lauryl bis-(2-hydroxy-ethyl)carboxy methyl betaine, stearyl bis-(2-hydroxy-propyl)carboxymethyl betaine, cocodimethyl sulfopropyl betaine, stearyldimethyl sulfopropyl betaine, lauryl dimethyl sulfoethyl betaine, lauryl bis-(2-hydroxy-ethyl)sulfopropyl betaine, cocoamidopropyl hydroxysultaine and mixtures thereof.

Nonionic surfactants are generally known and include, for example, alkanolamides, which may optionally be alkoxylated, amine oxides, fatty alcohols, which may optionally be alkoxylated, alkoxylated alkyl phenols, fatty acid esters, and alkylglucosides, such as cocamide DEA, cocamide MEA, cocamide MIPA, PEG-5 cocamide MEA, lauramide DEA, lauramine oxide, cocamine oxide, stearamine oxide, stearamidopropylamine oxide, palmitamidopropylamine oxide, decylamine oxide, stearyl alcohol, sorbitan monolaurate, polysorbates, ethoxylated lauryl alcohols, polyethylene glycol distearates, decyl glucosides, coco glucosides, dodecyl glucosides, octadecyl polyglucosides, and mixtures thereof.

In one embodiment, the personal care composition comprises, on 100 parts by weight of the composition, water, from about 2 to about 22 pbw, more typically from about 5 to about 15 parts by weight of a mixture of an anionic surfactant, such as one or more alkyl alkoxylated sulfates, and one or more nonionic surfactant, amphoteric surfactant and/or zwitterionic surfactant, such as a betaine surfactant, such mixture typically comprising from about 0.1 to about 20, more typically from about 0.5 to about 10, and still more typically from about 1 to about 8 pbw of the anionic surfactant per one pbw of the one or more nonionic, amphoteric surfactant, and/or zwitterionic surfactant.

In one embodiment, the personal care composition of the present invention is a "sulfate free" composition that is substantially free, more typically free of sulfate surfactant compounds, more typically free of any sulfate compounds. In one embodiment, the sulfate free personal care composition comprises one or more surfactants selected from amphoteric surfactants, nonionic surfactants, and non-sulfate anionic surfactants, such as, for example sulfonate surfactants, taurate surfactants, sulfosuccinate surfactants, sultaine surfactants, alkanolamide surfactants, sarcosinate surfactants, amine oxide surfactants, alkyl glucoside surfactants, phosphate ester surfactants, sorbital ester surfactants, ethoxylated alcohol surfactants, betaine surfactants, and amphoacetate surfactants. In one embodiment, a sulfate free composition comprises, based on 100 pbw of the surfactant mixture, from 5 to 15 pbw of a mixture of an a non-sulfate anionic surfactant or a mixture of a non-sulfate anionic surfactant and an amphoteric surfactant, such mixture typically comprising from about 5 to about 95 pbw of a non-sulfate anionic surfactant, such as a sulfosuccinate surfactant, and from about 5 to about 95 pbw of an amphoteric surfactant, such as a sultaine surfactant, and the personal care composition is free of sulfate surfactant compounds, typically free of any sulfate compounds. Typically, the polymer of the present invention provides good thickening performance and, in many cases, good yield strength and clarity, in such sulfate free compositions.

In one embodiment, the personal care composition further comprises, based on 100 pbw of the composition, from greater than 0 to about 30 pbw, more typically from about 0.1 to about 20 pbw, still more typically from about 0.25 to about 10 pbw, still more typically from about 0.5 pbw to about 6 pbw, of one or more non-surfactant electrolytes. Suitable non-surfactant electrolytes include, for example, alkali metal, alkaline earth, ammonium and substituted ammonium salts of inorganic acids, including, for example, calcium chloride, calcium carbonate, potassium chloride, sodium chloride, ammonium chloride, potassium iodide, sodium bromide, magnesium chloride, sodium sulfate, calcium nitrate, ammonium bromide, ammonium sulfate, ammonium nitrate.

In one embodiment, the personal care composition further comprises one or more personal care benefit agents. Suitable personal care benefit agents include materials that provide a personal care benefit, such as moisturizing, conditioning, or a sensory benefit, to the user of the personal care composition, such as, for example, emollients, conditioners, moisturizers, polymers, vitamins, abrasives, UV absorbers, antimicrobial agents, anti-dandruff agents, fragrances, and/or appearance modifying additives, such as, for example, colored particles or reflective particles, which may be in the form of a solid, liquid, or gas and may be insoluble or are only partly soluble in the personal care composition. Mixtures of the benefit agents may be used.

In one embodiment, the benefit agent comprises an oil benefit agent useful as an emollient, or conditioner for the skin or hair. Suitable oils, include for example, vegetable oils, such as arachis oil, castor oil, cocoa butter, coconut oil, corn oil, cotton seed oil, olive oil, palm kernel oil, rapeseed oil, safflower seed oil, sesame seed oil, and soybean oil, esters of $(C_{12}-C_{22})$carboxylic acids, such as butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, such as lanolin, mink oil, and tallow, hydrocarbon oils, such as mineral oils and petrolatum, and silicone oils, such as polydimethylsiloxanes, polydiethylsiloxanes, polymethylphenylsiloxanes, alkoxylated polyorganosiloxanes, amino-substituted polyorganosiloxanes, amido-substituted polyorganosiloxanes, and mixtures thereof.

In one embodiment, the benefit agent comprises a moisturizer. Suitable moisturizers include, for example, glycerin and hyaluronic acid.

In one embodiment, the benefit agent comprises a cationic polymer and/or an amphoteric polymer. Suitable cationic polymers include synthetic polymers that comprise monomeric units derived from one or more amine- and/or quaternary ammonium-substituted monomers and natural polymers that have been derivatized to include amine- and/or quaternary ammonium-containing pendant groups, each typically having a cationic charge density of from about 0.1 to 4 meq/g. Suitable cationic polymers include, for example, copolymers of 1-vinyl-2-pyrrolidine and 1-vinyl-3-methyl-imidazolium salts (such as Polyquaternium-16), copolymers of 1-vinyl-2-pyrrolidine and dimethylaminoethyl methacrylate (such as Polyquaternium-11), cationic diallyl quaternary ammonium-containing polymers including, for example, dimethyldiallylammonium chloride homopolymers and copolymers of acrylamide and dimethyldiallylammonium chloride (such as Polyquaternium 6 and Polyquaternium 7), cationic polyacrylamides, cationic polysaccharide polymers, such as, for example, cationic cellulose derivatives, cationic starch derivatives, and cationic guar gum derivatives, such as salts of hydroxyethyl cellulose reacted with trimethyl ammonium substituted epoxide (such as Polyquaternium 10), polymeric quaternary ammonium salts of hydroxyethyl cellulose reacted with lauryl dimethyl ammonium-substituted epoxide (such as Polyquaternium 24), guar hydroxypropyltrimonium chloride, hydroxypropyl guar hydroxypropyltrimonium chloride and cationic protein derivatives, such as cocodimonium hydroxypropyl hydrolyzed wheat protein. Suitable amphoteric polymers are polymers that contain both anionic groups, such as phosphate, phosphonate, sulphate, sulphonate or carboxylic acid groups, and cationic groups, such as tertiary amino groups or quaternary ammonium groups, on the same polymer molecule. Suitable amphoteric polymers include, for example, amphoteric acrylic copolymers, such as octylacrylamide/acrylate/butylaminoethyl methacrylate copolymers, and amphoteric polysaccharide compounds obtained by grafting and polymerization of cationic pendant groups, e.g., dimethyldiallylammonium chloride groups, onto anionic polysaccharide, for example, a sodium carboxymethyl-cellulose, backbone Aqueous compositions containing the polymer of the present invention, one or more surfactants and/or non-surfactants salts, and a cationic polymer and/or amphoteric polymer exhibit an enhanced thickening efficiency compared to analogous compositions that lack the cationic polymer and/or amphoteric polymer.

In one embodiment, the benefit agent comprises an anti-dandruff agent. Suitable anti-dandruff agents include, for example, particulate, crystalline anti-dandruff agents, such as sulfur, selenium disulfide, and heavy metal salts of pyridinethione, such as zinc pyrithione, as well as soluble anti-dandruff agents, such as ketoconazole.

In one embodiment, the benefit agent comprises a UV radiation absorber. Suitable UV radiation absorbers include, for example, sodium benzotriazolyl butylphenol sulfonate.

The personal care composition according to the present invention may optionally further comprise, based on 100 pbw of the personal care composition and independently for each such ingredient, up to about 10 pbw, typically from 0.1 pbw to about 8 pbw, and more typically from about 0.5 pbw to about 5.0 pbw, of other ingredients in addition to the one or more benefit agents, including, for example, preservatives such as benzyl alcohol, methyl paraben, propyl paraben and imidazolidinyl urea, pH adjusting agents such as citric acid, succinic acid, phosphoric acid, sodium hydroxide, sodium carbonate, dyes, and sequestering agents such as disodium ethylenediamine tetra-acetate. Other examples of ingredients commonly used in personal care compositions, which are suitable for use in the compositions of the present invention, are known and are described in, for example, in *Cosmetic Ingredient Handbook*, Eighth Edition, 2000.

In one embodiment, the personal care composition is a body wash that comprises, based on 100 pbw of the composition, from about 0.1 to about 5 pbw, more typically from about 0.5 to about 3 pbw, from of the polymer of the present invention, from about 1 to about 30 pbw, more typically from about 1 to about 20 pbw of one or more surfactants, more typically of a mixture of one or more anionic surfactants with one or more amphoteric surfactants, zwitterionic surfactants, and/or nonionic surfactants, optionally, one or more non-surfactant salts, and, optionally, one or more personal care benefit agents.

In one embodiment of the personal care composition, the polymer of the present invention is an effective thickener, that is, the polymer increases the viscosity of the personal care composition, that is responsive, but not overly sensitive, to salt content and or surfactant content, particularly at a pH of greater than or equal to 6.3, more typically greater than or equal to 6.5. More specifically, the viscosity of an aqueous composition comprising the polymer of the present invention typically increases with increasing surfactant content and/or non-surfactant salt content in a predictable and proportional manner and does not typically undergo undesirably large changes in viscosity in response to relatively small changes in the amount of surfactants and/or non-surfactant salts.

In one embodiment, the personal care composition of the present invention is a cream base hair colorant composition, comprising a liquid medium, a polymer according to the present invention, and a hair colorant, and optionally further comprising one or more of fatty acids, fatty acid esters, alkoxylated fatty acid esters, polyamines, and polysiloxanes. Suitable liquid media include, for example, water, one or more $(C_6-C_{22})$alcohols, which may optionally be alkoxylated, such as, for example, cetyl alcohol, stearyl alcohol, oleic alcohol, and mixtures thereof, Suitable hair colorants include, for example, dyes, oxidative azoic dyes, sulfur dyes, azomethine dyes, triarylmethane, xanthene dyes, phthalocyanin dyes, phenothiazine dyes, pigments, direct dyes, oxidation dyes, nacreous pigments, pearling agents, leuco dyes, visual lightening colorants, natural colorants, optically-variable pigments, and mixtures thereof.

In one embodiment of the personal care composition, the composition comprises an amount of the polymer of the present invention that is sufficient to impart a yield strength to the composition that is greater than 0 Pa, more typically of from about 0.01 Pa, and even more typically from about 0.1 to about 10 Pa, and even more typically from about 1 Pa to about 4 Pa, and even more typically from about 1 Pa to about 2 Pa. A non-zero yield strength is useful for suspending water insoluble particles in the personal care composition. As previously mentioned, the polymer of the present invention typically provides a yield strength of greater than 0 Pa, even in the absence of any cross-linking of the polymer.

In one embodiment, the liquid composition of the present invention comprises an amount of the polymer of the present invention, typically a non-crosslinked embodiment of such polymer, that is effective to impart a yield strength of greater than 1 Pa to the composition and the composition further comprises suspended particles of one or more solid, liquid, or gas that is insoluble or are only partly soluble in the personal care composition, such as, for example, abrasives, pigments, oil droplets, oil beads, liposomes, capsules, or gas bubbles. In one embodiment, the composition is stable and the particles remain suspended in the composition for an extended time period, such as, for example greater than 6 months, more typically greater than one year 1 year at ambient temperature, as well as under accelerated aging conditions, such as, for example, greater than 3 months storage at 45° C. In one embodiment, the suspended particles comprise droplets of an oil benefit agent.

In one embodiment of the personal care composition wherein the personal care composition has a pH of greater than or equal to 6.5, the polymer of the present invention provides thickening properties and imparts a non-zero yield strength in the presence of surfactant without imparting an visually turbid appearance to the composition, thus allowing formulation of visually clear, viscous compositions having a non-zero yield strength.

In one embodiment of the personal care composition, typically wherein the personal care composition has a pH of greater than or equal to about 6.5, the polymer of the present invention provides thickening properties and imparts a non-zero yield strength in the presence of surfactants and/or non-surfactant salts and the composition clear, transparent visual appearance, for example, a transmittance at 600 nm of greater than 95%.

In one embodiment of the personal care composition, typically wherein the personal care composition has a pH of less than about 6.5, the polymer of the present invention provides thickening properties and imparts a non-zero yield strength in the presence of surfactants and/or non-surfactant salts, and imparts an opaque visual appearance to the composition. Also, a higher yield strength can typically be obtained with given polymer content at a pH of less than 6, compared to a composition having a pH of greater than or equal to 6.5.

In one embodiment of the personal care composition, the polymer of present invention provide enhanced foam volume and enhanced foam stability, resulting in a higher foam volume that decreases more slowly, and that exhibits improved sensory properties such as improved whiteness, shininess, firmness, elasticity, and apparent wetness.

In one embodiment of the personal care composition, the polymer of the present invention provides high foam volume. In an embodiment of the personal care composition that comprises a cationic polymer, the polymer of the present invention provides high foam volume and reduces drainage, resulting in a wet, creamy, shiny, white foam. In one embodiment of the personal care composition, the combination of the polymer of present invention and cationic polymer provide enhanced foam firmness and elasticity, resulting in a foam that exhibits improved sensory properties, such as improved density, richness, and cushiony feeling.

In one embodiment of the personal care composition, the polymer of the present invention provides good sensory properties, such as, for example a smooth, velvety feel and a lack of tacky feeling on the skin.

In one embodiment of the personal care composition, the polymer of the present invention is easily rinsed from the skin with water, leaving minimal or no perceptible polymer residue on the skin.

In one embodiment, the present invention is directed to a home care composition or institutional or industrial cleaning composition, such as a liquid detergent, a laundry detergent, a hard surface cleanser, a dish wash liquid, or a toilet bowl cleaner, comprising water, one or more surfactants, and a polymer of the present invention. Suitable home care composition or institutional or industrial cleaning compositions include, surface cleansers for kitchen and bathroom counter tops, tiled surfaces, and utilities, including appliances employed or located therein, toilet cleaners, including toilet bowl rim gels, floor cleansers, wall cleansers, polishes, air freshener gels, detergents, treatments and cleansers for dishes and laundry, such as fabric softener, spot reducer, and fabric treatments. Suitable surfactants include those described above in regard to the personal care composition embodiments of the present invention. Such cleaning compositions may optionally further comprise one or more of water miscible organic solvents, such as alcohols and glycols, and/or one or more additives. Suitable additives are known in the art and include, for example, organic builders, such as organophosphonates, inorganic builders, such as ammonium polyphosphates, alkali metal pyrophosphates, zeolites, silicates, alkali metal borates, and alkali metal carbonates, bleaching agents, such as perborates, percarbonates, and hypochlorates, sequestering agents and anti-scale agents, such as citric acid and ethylenediaminetetraacetic acid, inorganic acids, such as phosphoric acid and hydrochloric acid, organic acids, such as acetic acid, organic bases, inorganic bases, such as NaOH, abrasives, such as silica or calcium carbonate, antibacterial agents or disinfectants, such as triclosan and cationic biocides, for example (N-alkyl)benzyldimethylammonium chlorides, fungicides, enzymes, opacifing agents, pH modifiers, dyes, fragrances, and preservatives.

In one embodiment, the home care composition or institutional or industrial care composition comprises, based on 100 pbw of the personal care composition, from about 5 to about 80 pbw, more typically from about 10 to about 70 pbw, of a liquid medium, typically an aqueous liquid medium, from greater than 0 to about 40 pbw, more typically from greater than 0 to 20, even more typically from about 0.05 to about 10 pbw, and still more typically from about 0.1 to about 5 pbw, of the polymer of the present invention, and from greater than 0 to about 20 pbw of one or more surfactants, and, optionally, one or more additives selected from builders, bleaching agents, acids, bases, or abrasives, antibacterial agents, fungicides, enzymes, opacifing agents, pH modifiers, dyes, fragrances, and preservatives.

Examples 1-3

The polymers of Examples 1, 2 and 3 were each made according to the procedure set forth below.

Water and a sulfated alcohol ethoxylate (Rhodapex AB20, Rhodia Inc.) were charged to a reaction vessel and heated to about 65° C., while purging with $N_2$. A $N_2$ blanket was maintained throughout each run. When the temperature reached about 65° C., a 25% of Initiator solution and 2% of monomer emulsion were added to the reaction vessel. The temperature was then maintained at about 65° C. for about 15 minutes. The remaining monomer emulsion and initiator solution were fed into the reaction vessel at a steady rate over 3 hours. Once the monomer and initiator feeds were completed, the contents of the reaction vessel were maintained at about 65° C. for about 1 hour and then a chaser solution consisting of t-butylperoxy benzoate added to the reaction vessel in one shot, followed by continuous addition of erythorbic acid solution over 30 minutes, was introduced to the reaction vessel. Once introduction of the chaser solution was completed, the contents of the reaction vessel were maintained at about 65° C. for 90 minutes, and then allowed to cool.

The ingredients used are summarized in TABLE I below. The polymers of Examples 1, 2 and 3, each contained:

first monomeric units derived from a monomeric compound according to structure (XII) above, wherein $R^{19}$=methyl, i=25, and j=5 ("NOPOL polyether monomer"), second monomeric units derived from a mixture of ($C_{16}$-$C_{22}$)alkyl-polyethoxylated methacrylates having an average of 25 ethylene oxide units per molecule, according to structure (XX), wherein $R^{24}$ is methyl, $R^{21}$ is a mixture of linear $C_{16}$ alkyl, linear $C_{18}$ alkyl, and linear $C_{22}$ alkyl groups, p=2, r=25 s=0, and t=1 ("($C_{16}$-$C_{22}$)alkyl-polyether monomer"), third monomeric units derived from methacrylic acid ("MAA"), and fourth monomeric units derived from ethyl acrylate ("EA").

The NOPOL polyether monomer was introduced in the form of an aqueous solution ("NOPOL polyether monomer solution") that contained, based on 100 pbw of the solution, about 50 pbw of the NOPOL polyether monomer and about 25 pbw MAA. The ($C_{16}$-$C_{22}$)alkyl-polyether monomer was introduced in the form of an aqueous solution ("($C_{16}$-$C_{22}$) alkyl-polyether solution") that contained, based on 100 pbw of the solution, about 50 pbw of the ($C_{16}$-$C_{22}$)alkyl-polyether monomer and about 25 pbw MAA.

TABLE I

| | Charges (g) | | |
|---|---|---|---|
| | Ex 1 | Ex 2 | Ex 3 |
| Kettle charge | | | |
| Water | 323.9 | 322.8 | 382.8 |
| Rhodapex AB20 (sulfated alcohol ethoxylate, 29% solids content) | 2.07 | 5.17 | 2.07 |
| Monomer solution | | | |
| Water | 300.0 | 300.0 | 300.0 |
| Rhodapex AB20 (sulfated alcohol ethoxylate, 29% solids content) | 20.7 | 51.7 | 20.7 |

TABLE I-continued

| | Charges (g) | | |
|---|---|---|---|
| | Ex 1 | Ex 2 | Ex 3 |
| EA | 159.0 | 159.0 | 144.0 |
| MAA | 111.0 | 111.0 | 96.0 |
| NOPOL polyether monomer solution | 24.0 | 24.0 | 60.0 |
| ($C_{16}$-$C_{22}$) alkyl-polyether monomer solution | 36.0 | 36.0 | 60.0 |
| Initiator solution | | | |
| Ammonium persulfate | 0.84 | 0.84 | 0.42 |
| Water | 79.7 | 79.7 | 39.8 |
| Chaser solution Part 1: | | | |
| t-butylperoxybenzoate | 0.60 | 0.60 | 0.60 |
| Part 2: | | | |
| Water | 19.7 | 19.7 | 19.7 |
| Erythorbic acid | 0.30 | 0.30 | 0.30 |
| Total | 1077.8 | 1110.8 | 1126.4 |

The relative amounts of the monomeric units in the each of the respective polymers of Examples 1, 2 and 3 are given in TABLE II below, as weight percent of the respective monomers, based on the total amount of monomers charged to the reactor and as mole percent of the respective monomers, based on the total amount of monomers charged to the reactor. The average particle size, as determined by light scattering, of each of the latex polymers of Examples 1, 2, and 3 are also given in TABLE II.

TABLE II

| | Ex 1 | Ex 2 | Ex 3 |
|---|---|---|---|
| NOPOL polyether monomer | | | |
| wt % | 3.8 | 3.8 | 9.1 |
| mole % | 0.3 | 0.3 | 0.7 |
| ($C_{16}$-$C_{22}$) alkyl-polyether monomer | | | |
| wt % | 5.7 | 5.7 | 9.1 |
| mole % | 0.4 | 0.4 | 0.7 |
| MAA | | | |
| wt % | 40.00 | 40.00 | 38.2 |
| mole % | 47.6 | 47.6 | 49.8 |
| EA | | | |
| wt % | 50.5 | 50.5 | 43.6 |
| mole % | 51.7 | 51.7 | 48.9 |
| Average particle size (nm) | 103 | 71 | 94 |

Examples F1-1 to F1-11 and Comparative Examples CF1-1 to CF1-3

The body wash compositions F1-1 to F1-8 were prepared as follows. The polymer of Example 1 was added to deionized water under moderate agitation. Sodium laureth-2EO sulfate ("SLES", as Rhodapex ESB 3/A2) was then added, followed by slow addition of a solution of sodium hydroxide (15%) to the mixture, so as to reach a solution pH of from about 9 to about 10. Cocamidopropylbetaine ("CAPB", as Mirataine BET C-30) was then added, followed by preservative and sodium chloride. The pH of the composition was then adjusted to within a range of from 5 to 7 with a solution of citric acid (15%). Formula compositions are given in TABLE III in pbw ingredient per 100 pbw of the composition, wherein the notation "q.s" in this and in the following Examples indicate a "quantum sufficiat", that is, a sufficient quantity of a given material to achieve a given purpose, typically pH adjustment, for example, a sufficient quantity of NaOH to achieve the desired pH.

TABLE III

|  | F1-1 to F1-5 (pbw/ 100 pbw) | F1-6 (pbw/ 100 pbw) | F1-7 (pbw/ 100 pbw) | F1-8 (pbw/ 100 pbw) |
| --- | --- | --- | --- | --- |
| Polymer of Ex 1 | 2.0 | 1.5 | 2.0 | 2.5 |
| SLES | 9.0 | 9.0 | 9.0 | 9.0 |
| NaOH (15%) | q.s | q.s | q.s | q.s |
| CAPB | 2.0 | 2.0 | 2.0 | 2.0 |
| Preservative (Kathon CG) | 0.05 | 0.05 | 0.05 | 0.05 |
| NaCl | 0.5 | 0.5 | 0.5 | 0.5 |
| Citric Acid (15%) | q.s | q.s | q.s | q.s |
| Deionized Water | to 100 | to 100 | to 100 | to 100 |

Rheological measurements were conducted on a TA instruments AR2000 Rheometer at 20° C. A 60 mm, 2° cone was used, with a cone/plate gap of 53 micrometers. After a conditioning step at 20° C. with an equilibrium duration of 2 min, a stepped flow step was applied with a ramp shear rate from $10^{-3}$ sec$^{-1}$ to 1.0 sec−1, 20 points per decade, with a contact time of 10 sec. A continuous ramp step was applied from shear rate between 1.0 sec$^{-1}$ and 200 sec$^{-1}$. The yield strength was determined as the limiting value of the applied shear stress when the sample started to flow. Brookfield Viscosity of the compositions were measured using a Brookfield Viscometer Model DVD-I or DVII+ at 10 RPM.

The pH and yield strength, expressed in Pascals ("Pa"), and viscosity, in centiPoise ("cP"), as measured using a Brookfield viscoscometer at 10 revolutions per minute, for each of the compositions of Examples F1-1 to F1-5 are given in TABLE IV below. All viscosity measurements given in this and the following Examples are at 20° C., unless other wise noted.

TABLE IV

| Ex # Body Wash 1 (SLES/CAPB) | Polymer Content (pbw/100 pbw) | pH | Yield Strength (Pa) | Viscosity cP |
| --- | --- | --- | --- | --- |
| F1-1 | 2.0 | 5.2 | 2.1 | 6680 |
| F1-2 | 2.0 | 5.5 | 1.6 | 6940 |
| F1-3 | 2.0 | 6.1 | 0.4 | 3380 |
| F1-4 | 2.0 | 6.5 | 0.4 | 8080 |
| F1-5 | 2.0 | 7.0 | 0.4 | 14080 |

The yield strength exhibited by the body wash composition of Examples F1-1 to F1-5 was found to be stable at about 0.4 Pa for pH from about 7 to about 6 and to increase with decreasing pH for pH below about 6. The Brookfield Viscosity exhibited by the body wash composition of Examples F1-1 to F1-5 was found to increase with pH above pH 6.1.

The Brookfield Viscosity, as measured at 10 RPM and expressed in centiPoise ("cP"), and yield strength, expressed in Pascals ("Pa"), for each of the compositions of Examples F1-6 to F1-8 are given in TABLE V below.

TABLE VI

| Ex # | Polymer Content (pbw/100 pbw) | Brookfield Viscosity at 10 rpm (cP) | Yield Strength (Pa) |
| --- | --- | --- | --- |
| F1-6 | 1.5 | 4160 | 0.79 |
| F1-7 | 2.0 | 9960 | 2.07 |
| F1-8 | 2.5 | 13800 | 3.14 |

The viscosity and yield strength of the body wash composition of Examples F1-6 to F1-8, adjusted to a final pH of about 5.0 to 5.1, were found to be very responsive to the amount of polymer of Example 1, within the range of from 1.5 to 2.5 active % Wt in the body wash composition.

The body wash compositions F1-9 to F1-11 and Comparative Examples CF1-1 to CF1-3 were made in a manner analogous to that described above in regard to Examples F1-1 to F1-8, but using different relative amounts of sodium chloride and the polymer of Example 1, as summarized in TABLE VI. Final formulation pH was adjusted to about 6.5. The body wash compositions of Examples CF1-1 to CF1-3 were made in a manner analogous to that described above in regard to Examples F1-1 to F1-8, except that a crosslinked acrylic rheology modifier polymer, Carbopol® Aqua SF-1 (Lubrizol Corporation, "SF-1"), was substituted for the polymer of Example 1, and the pH of the composition was adjusted to 6.5 by slow addition of a solution of sodium hydroxide (15%). prior to addition of the CAPB, preservative, and sodium chloride. Final formulation pH was adjusted to pH about 6.5 with a solution of citric acid (15%). Formula compositions are given in TABLE VII below in pbw ingredient per 100 pbw of the composition.

TABLE VII

| Material | F1-9 (pbw/ 100 pbw) | F1-10 (pbw/ 100 pbw) | F1-11 (pbw/ 100 pbw) | CF1-1 (pbw/ 100 pbw) | CF1-2 (pbw/ 100 pbw) | CF1-3 (pbw/ 100 pbw) |
| --- | --- | --- | --- | --- | --- | --- |
| Polymer of Ex 1 | 2.0 | 2.0 | 2.0 | — | — | — |
| SF-1 | — | — | — | 2.0 | 2.0 | 2.0 |
| SLES | 9.0 | 9.0 | 9.0 | 9.0 | 9.0 | 9.0 |
| NaOH (15%) to pH 9-10 | q.s | q.s | q.s | q.s | q.s | q.s |
| CAPB | 2.0 | 2.0 | 2.0 | 2.0 | 2.0 | 2.0 |
| Preservative (Kathon CG) | 0.05 | 0.05 | 0.05 | 0.05 | 0.05 | 0.05 |
| NaCl | 0.0 | 0.5 | 1.6 | 0.0 | 0.5 | 1.6 |
| Citric Acid (15%) to pH 6.5 | q.s | q.s | q.s | q.s | q.s | q.s |
| Deionized Water | to 100 | to 100 | to 100 | to 100 | to 100 | to 100 |

The viscosity, expressed in centiPoise ("cP"), as measured using a Brookfield Viscometer at 10 RPM, and percent transmittance (%), as measured at 600 nm in a 10×10 mm cell, were determined for each of the compositions of Examples F1-9 to F1-11 and are reported in TABLE VIII below.

TABLE VIII

| Ex # | Polymer Content (pbw/100 pbw) | Sodium Chloride Content (pbw/100 pbw) | Brookfield Viscosity at 10 rpm (cP) | Transmittance at 600 nm (%) |
| --- | --- | --- | --- | --- |
| F1-9 | 2.0 | 0 | 5320 | 99.6 |
| F1-10 | 2.0 | 0.5 | 11960 | 98.6 |
| F1-11 | 2.0 | 1.6 | 78500 | 98.4 |
| CF1-1 | 2.0 | 0 | 2300 | 96.6 |
| CF1-2 | 2.0 | 0.5 | 3340 | 94.1 |
| CF1-3 | 2.0 | 1.6 | 9860 | 87.8 |

The viscosity of the body wash compositions of Examples F1-9 to F1-11, each adjusted to a final pH of 6.5, were found to increase drastically with the increasing amount of sodium chloride in the body wash composition, within the range of from 0 to 1.6 active % sodium chloride. A high visual clarity, as indicated by a transmittance at 600 nm of greater than 95%, was obtained for Examples F1-9 to F1-11 within the range of from 0 to 1.6 pbw sodium chloride per 100 pbw of the composition. The viscosity of the body wash compositions of Comparative Examples CF1-1 to CF1-3 containing CA SF-1 polymer were lower in comparison with Examples F1-9 to F1-11. Visual clarity as indicated by a transmittance at 600 nm of Comparative Examples CF1-1 to CF1-3, containing CA SF-1 polymer, decreases with increasing sodium chloride content. A higher visual clarity was obtained for body wash compositions containing the polymer of Example 1 than for an analogous shampoo composition containing SF-1 polymer at the same amount of polymer content.

Example 4 and Comparative Examples C1-C4

The polymers of Examples 4 to 17 and Comparative Examples $C_1$-$C_4$ were made in a manner analogous to that described above in regard to Examples 1-3 using different relative amounts of the respective monomers as summarized in TABLE IX, parts A and B, below (as wt % of the respective monomers, based on the total amount of monomers charged to the reactor). The polymers of Examples 15, 16, and 17 were each crosslinked using either ethylene glycol dimethacrylate ("EGDMA") or polyethyleneglycol 400 dimethacrylate (PEG400DMA Li).

Example F2 and Comparative Examples CF2-1 to CF2-3

The performance of the polymer of Example 4 was compared with that of the polymer Comparative Example C1, the polymer of Comparative Example C2, and a 50:50 blend of the polymer of Comparative Example C1 and the polymer of Comparative Example C2 in series of analogous aqueous body wash compositions, each comprising, based on 100 pbw of the body wash composition, 3.28 pbw ammonium lauryl sulfate ("ALES"), 0.41 pbw cocamide monoethanolamine ("CMEA"), and 0.82 pbw cocoamidopropyl betaine ("CAPB") and a total polymer content of 2.5 pbw, and having a pH of 6.5. Viscosity was measured using a TA Instrument Rheometer Model AR-G2 using a 40 mm, 4° cone with a 116 micron cone/plate gap and yield strength was determined by extrapolating the shear stress to a zero shear rate on a plot of shear stress versus shear rate. The results are set forth in TABLE X below, as yield strength (in Pascals ("Pa"), and viscosity (in Pascal seconds ("Pa·s") at various shear rates (in reciprocal seconds, "$s^{-1}$").

TABLE X

| Ex # | Polymer of Ex#/ | Yield | Viscosity, η, at Shear rate | |
|---|---|---|---|---|
| Body Wash 2 (ALES/CMEA/CAPB) | pbw per 100 pbw | Strength (Pa) | η (Pa·s) | Shear rate (sec$^{-1}$) |
| F2 | 4/2.5 | 2.5 | 3155 | 0.001 |
|  |  |  | 678 | 0.01 |
|  |  |  | 182 | 0.1 |
|  |  |  | 73 | 1 |
|  |  |  | 10 | 10 |
| CF 2-1 | C1/2.5 | 0.9 | 1003 | 0.001 |
|  |  |  | 169 | 0.01 |

TABLE IX

A.

| Monomer | Ex 4 (wt %) | Ex 5 (wt %) | Ex 6 (wt %) | Ex 7 (wt %) | Ex 8 (wt %) | Ex 9 (wt %) | Ex 10 (wt %) | Ex 11 (wt %) | Ex 12 (wt %) |
|---|---|---|---|---|---|---|---|---|---|
| NOPOL polyether | 4.76 | 6.60 | 3.81 | 3.77 | 3.74 | 1.94 | 3.85 | 5.71 | 5.61 |
| ($C_{16}$-$C_{22}$) alkyl polyether | 4.76 | 4.72 | 5.71 | 7.55 | 9.35 | 3.88 | 3.85 | 3.81 | 7.48 |
| MAA | 40.00 | 39.79 | 40.00 | 39.79 | 39.58 | 40.43 | 40.21 | 40.00 | 39.58 |
| EA | 50.48 | 48.89 | 50.48 | 48.89 | 47.33 | 53.74 | 52.09 | 50.48 | 47.33 |
| EGDMA | — | — | — | — | — | — | — | — | — |
| PEG400DMA Li | — | — | — | — | — | — | — | — | — |

B.

| Monomer | Ex 13 (wt %) | Ex 14 (wt %) | Ex 15 (wt %) | Ex 16 (wt %) | Ex 17 (wt %) | Ex 18 (wt %) | Ex 19 (wt %) | Ex 20 (wt %) | Ex 21 (wt %) |
|---|---|---|---|---|---|---|---|---|---|
| NOPOL polyether | 7.51 | 9.30 | 3.87 | 3.80 | 5.75 | 4.88 | 0 | 9.52 | 0.00 |
| ($C_{16}$-$C_{22}$) alkyl polyether | 4.69 | 4.65 | 1.94 | 5.71 | 1.92 | 0 | 4.88 | 0.00 | 9.52 |
| MAA | 39.69 | 39.48 | 40.31 | 39.94 | 40.10 | 41.46 | 41.46 | 40.00 | 40.00 |
| EA | 48.11 | 46.56 | 53.58 | 50.40 | 51.94 | 53.66 | 53.66 | 50.48 | 50.48 |
| EGDMA | — | — | 0.31 | — | — | — | — | — | — |
| PEG400DMA Li | — | — | — | 0.15 | 0.29 | — | — | — | — |

TABLE X-continued

| Ex # Body Wash 2 (ALES/CMEA/CAPB) | Polymer of Ex#/ pbw per 100 pbw | Yield Strength (Pa) | Viscosity, η, at Shear rate | |
|---|---|---|---|---|
| | | | η (Pa·s) | Shear rate (sec$^{-1}$) |
| | | | 31 | 0.1 |
| | | | 7 | 1 |
| | | | 2 | 10 |
| CF 2-2 | C2/2.5 | 0.1 | 391 | 0.001 |
| | | | 204 | 0.01 |
| | | | 114 | 0.1 |
| | | | 78 | 1 |
| | | | 45 | 10 |
| CF 2-3 | C1/1.25 and C2/1.25 | 0.15 | 287 | 0.001 |
| | | | 99 | 0.01 |
| | | | 32 | 0.1 |
| | | | 12 | 1 |
| | | | 7 | 10 |

Compared with analogous body wash compositions that contained the polymer of Comparative Example C1, the polymer of Comparative Example C2, or a 50:50 blend of the polymer of Comparative Example C1 and the polymer of Comparative Example C2, the composition that contained the polymer of Example 4 exhibited a higher yield strength, a higher viscosity at low shear rates, and more pronounced shear thinning behavior at the same amount of total polymer content.

Example F3 and Comparative Examples CF3-1 to CF3-5

The performance of the polymer of Example 4 was compared with that of the polymer of Comparative Example C1, the polymer of Comparative Example C2, the polymer of Comparative Example C3, the polymer of Comparative Example C4, and a 50:50 blend of the polymer of Comparative Example C1 and the polymer of Comparative Example C2 in analogous aqueous body wash compositions of Comparative Examples CF3-1 to CF3-5, each comprising, based on 100 pbw of the composition, 9 pbw sodium laureth-2 sulfate ("SLES"), and 2 pbw cocoamidopropyl betaine ("CAPB"), and a total polymer content of 2.5 pbw and having a pH of 6.5. The body wash formulations F3, CF3-1, CF3-2, CF3-3, CF3-4, and CF3-5, were prepared in a manner analogous to that described above in regard to Examples F1-1 to F1-8. Viscosity and yield strength were determined as described above in regard to Example F1-1 to F1-11. Transmittance at 600 nm was measured as described above in regard to Examples F1-9 to F1-11. The results are set forth in TABLE XI below, as transmittance (%) at 600 nm, yield strength (in Pascals ("Pa")), viscosity (in Pascal seconds ("Pa·s")) at various shear rates (in reciprocal seconds ("s$^{-1}$")), and Brookfield Viscosity at 10 RPM in centipoise ("cP").

TABLE XI

| Ex# Body Wash 3 (SLES/CAPB) | Polymer of Ex#/ (pbw/ 100 pbw) | Transmit-tance (%) | Yield Strength (Pa) | Brookfield Viscosity 10 RPM (cP) | Viscosity, η at Shear rate | |
|---|---|---|---|---|---|---|
| | | | | | n (Pa.s) | Shear rate (sec$^{-1}$) |
| F3 | 4/2.5 | 99 | 0.95 | 11440 | 137.16 | 0.002 |
| | | | | | 69.62 | 0.01 |
| | | | | | 22.94 | 0.10 |
| | | | | | 10.39 | 1 |
| CF3-1 | C1/2.5 | 95.8 | 0.17 | 1500 | 3.41 | 0.002 |
| | | | | | 3.21 | 0.01 |
| | | | | | 2.53 | 0.10 |
| | | | | | 1.09 | 1 |
| CF3-2 | C2/2.5 | 98.7 | 0.13 | 24200 | 55.96 | 0.002 |
| | | | | | 48.94 | 0.01 |
| | | | | | 32.10 | 0.10 |
| | | | | | 22.35 | 1 |
| CF3-3 | C1/1.25 and C2/1.25 | 94.5 | 0.15 | 4640 | 21.02 | 0.002 |
| | | | | | 20.29 | 0.01 |
| | | | | | 12.85 | 0.10 |
| | | | | | 7.08 | 1 |
| CF3-4 | C3/2.5 | 96.7 | 0.45 | 2140 | 4.51 | 0.002 |
| | | | | | 4.27 | 0.01 |
| | | | | | 3.02 | 0.10 |
| | | | | | 1.16 | 1 |
| CF3-5 | C4/2.5 | 98.6 | 2.2 | 170000 | 606.63 | 0.002 |
| | | | | | 451.80 | 0.01 |
| | | | | | 254.30 | 0.10 |
| | | | | | 152.20 | 1 |

Compared with analogous body wash compositions that contained the polymer of Comparative Example C1, the polymer of Comparative Example C2, the polymer of Comparative Example C3, the polymer of comparative example C4, or a 50:50 blend of the polymer of Comparative Example C1 and the polymer of Comparative Example C2, composition that contained the polymer of Example 4 exhibited a higher visual clarity (as indicated by higher % transmittance) at the same amount of total polymer content. Compared with analogous body wash compositions that contained the polymer of Comparative Example C1, the polymer of Comparative Example C2, the polymer of Comparative Example C3, or a 50:50 blend of the polymer of Comparative Example C1 and the polymer of Comparative Example C2, the composition that contained the polymer of Example 4 exhibited a higher yield strength at the same amount of total polymer content. Compared with analogous body wash compositions that contained the polymer of Comparative Example C1, the polymer of Comparative Example C3, or a 50:50 blend of the polymer of Comparative Example C1 and the polymer of Comparative Example C2, the composition that contained the polymer of Example 4 exhibited a higher Brookfield viscosity at 10 RPM, a higher viscosity at low shear rates, and more pronounced shear thinning behavior, at the same amount of total polymer content. The polymer of Example 4 exhibited a desirable balance of yield strength, Brookfield Viscosity at 10 RPM, shear thinning behavior, and high visual clarity for use in the body wash application.

Examples F4-1 to F4-7

The 2-in-1 shampoo compositions of F4-1 to F4-7 were made as follows: Part A of the shampoo was prepared by adding the polymer latex of Example 1 to deionized water under moderate agitation. Sodium laureth-2EO sulfate ("SLES", as Rhodapex ESB 3/A2) was added, followed by slow addition of aqueous sodium hydroxide (15%) to a pH of from 9 to 10. Cocamidopropylbetaine ("CAPB", as Mirataine BET C-30) was then added, and formulation pH was adjusted with aqueous citric acid (15%) to 6.5. Part B of the shampoo was made by sprinkling in guar hydroxypropyltrimonium chloride (Jaguar Excel) in deionized water under agitation. Once the cationic guar is completely dispersed, the pH of part B was adjusted between 4 and 5 with aqueous citric acid (15%). Part B was admixed to Part A, and preservative, sodium chloride were added. Final formulation pH was adjusted to 6.5 with aqueous citric acid (15%). Compositions are given in TABLE XII below in as pbw of each ingredient per 100 pbw of the shampoo composition The viscosity, as measured using a Brookfield viscometer at 10 RPM, is set forth in TABLE XIII below, in centiPoise ("cP"), for each of the shampoo compositions.

TABLE XII

|  | Ex F4-1 (pbw/ 100 pbw) | Ex F4-2 (pbw/ 100 pbw) | Ex F4-3 (pbw/ 100 pbw) | Ex F4-4 (pbw/ 100 pbw) | Ex F4-5 (pbw/ 100 pbw) | Ex F4-6 (pbw/ 100 pbw) |
|---|---|---|---|---|---|---|
| Part A |  |  |  |  |  |  |
| Deionized water | 20.0 | 20.0 | 20.0 | 20.0 | 20.0 | 20.0 |
| Polymer of Ex 1 | 0.0 | 2.0 | 2.0 | 0.0 | 1.0 | 1.0 |
| SLES | 9.0 | 9.0 | 9.0 | 9.0 | 9.0 | 9.0 |
| NaOH (15%) to 9 ≤ pH ≤ 10 | q.s | q.s | q.s | q.s | q.s | q.s |
| CAPB | 2.0 | 2.0 | 2.0 | 2.0 | 2.0 | 2.0 |
| Citric Acid (15%) to pH 6.5 | q.s | q.s | q.s | q.s | q.s | q.s |
| Part B |  |  |  |  |  |  |
| Deionized water | 28.0 | 28.0 | 28.0 | 28.0 | 28.0 | 28.0 |
| Jaguar Excel | 0.2 | 0.0 | 0.2 | 0.2 | 0.0 | 0.2 |
| Citric Acid (15%) | q.s | q.s | q.s | q.s | q.s | q.s |
| Preservative (Kathon CG) | 0.05 | 0.05 | 0.05 | 0.05 | 0.05 | 0.05 |
| Sodium Chloride | 0.5 | 0.5 | 0.5 | 1.6 | 1.6 | 1.6 |
| Deionized Water | to 100 | to 100 | to 100 | to 100 | to 100 | to 100 |

TABLE XIII

| Ex # | Polymer of Ex 1 (pbw per 100 pbw) | Jaguar EXCEL (pbw per 100 pbw) | Sodium Chloride (pbw per 100 pbw) | Brookfield Viscosity at 10 rpm (cP) |
|---|---|---|---|---|
| F4-1 | 0.0 | 0.2 | 0.5 | 80 |
| F4-2 | 2.0 | 0.0 | 0.5 | 11960 |
| F4-3 | 2.0 | 0.2 | 0.5 | 25680 |
| F4-4 | 0.0 | 0.2 | 1.6 | 460 |
| F4-5 | 1.0 | 0.0 | 1.6 | 10460 |
| F4-6 | 1.0 | 0.2 | 1.6 | 18880 |

The Brookfield viscosity of the 2-in-1 shampoo composition of Example F4-3 was unexpectedly higher than the sum of viscosity of 2-in-1 shampoo compositions of Examples F4-1 and F4-2. The Brookfield viscosity of the 2-in-1 shampoo composition of Example F4-6 was unexpectedly higher than the sum of viscosity of 2-in-1 shampoo compositions of Examples F4-4 and F4-5. While not wishing to be bound by theory, it appears that the unexpected increase in viscosity is due to interaction of the polymer of Example 1 and Jaguar Excel in the 2-in-1 shampoo compositions F4-3 and F4-6.

Examples F5-1 to F5-5

The 2-in-1 Shampoo compositions F5-1 to F5-5 were prepared as follows. Part A of the shampoo was prepared by adding the polymer latex of Example 1 or SF-1 polymer, to deionized water under moderate agitation. Sodium laureth-2EO sulfate ("SLES", Rhodapex ESB 3/A2) was added, followed by slow addition of aqueous sodium hydroxide (15%) to a pH of from 6.5 to 10. Cocamidopropylbetaine ("CAPB", Mirataine BET C-30) was then added, and formulation pH was adjusted with aqueous citric acid (15%) to 6.5. Part B was prepared by adding Polyquaternium-7 ("PQ-7", as Mirapol 550) in deionized water under agitation. Part B was admixed to Part A, and preservative, sodium chloride were added. Final formulation pH was adjusted to 6.5 with aqueous citric acid (15%). The ingredients and their relative amounts are listed in TABLE XIV below, as pbw of the active ingredient per 100 pbw of the shampoo composition. The percent transmittance (%), as measured at 600 nm in a 10×10 mm cell and viscosity, in centiPoise ("cP") as measured using a Brookfield viscometer at 10 RPM, for each of the compositions of Examples F5-1 to F5-5 are given in TABLE XV below.

TABLE XIV

|  | Ex F5-1 (pbw per 100 pbw) | Ex F5-2 (pbw per 100 pbw) | Ex F5-3 (pbw per 100 pbw) | Ex F5-4 (pbw per 100 pbw) | Ex F5-5 (pbw per 100 pbw) |
|---|---|---|---|---|---|
| Part A |  |  |  |  |  |
| Deionized water | 20.0 | 20.0 | 20.0 | 20.0 | 20.0 |
| Polymer of Ex 1 | 0.0 | 1.0 | 1.0 | 0.0 | 0.0 |
| SF-1 | 0.0 | 0.0 | 0.0 | 1.0 | 1.0 |
| SLES | 9.0 | 9.0 | 9.0 | 9.0 | 9.0 |
| NaOH (15%) to 9 ≤ pH ≤ 10 | q.s | q.s | q.s | q.s | q.s |
| CAPB | 2.0 | 2.0 | 2.0 | 2.0 | 2.0 |
| Citric Acid (15%) to pH 6.5 | q.s | q.s | q.s | q.s | q.s |
| Part B |  |  |  |  |  |
| Deionized water | 28.0 | 28.0 | 28.0 | 28.0 | 28.0 |
| PQ-7 | 0.2 | 0.0 | 0.2 | 0.0 | 0.2 |
| Citric Acid (15%) | q.s | q.s | q.s | q.s | q.s |
| Preservative (Kathon CG) | 0.05 | 0.05 | 0.05 | 0.05 | 0.05 |
| NaCl | 1.6 | 1.6 | 1.6 | 1.6 | 1.6 |
| Deionized Water | to 100 | to 100 | to 100 | to 100 | to 100 |

TABLE XV

| Ex # | Polymer of EX 1 (pbw per 100 pbw) | SF-1 polymer (pbw per 100 pbw) | PQ-7 (pbw per 100 pbw) | Transmittance at 600 nm (%) | Brookfield Viscosity at 10 rpm (cP) |
|---|---|---|---|---|---|
| F5-1 | 0.0 | 0.0 | 0.2 | 99.2 | 140 |
| F5-2 | 1.0 | 0.0 | 0.0 | 98.7 | 10460 |
| F5-3 | 1.0 | 0.0 | 0.2 | 97.3 | 13600 |
| F5-4 | 0.0 | 1.0 | 0.0 | 80.0 | 2380 |
| F5-5 | 0.0 | 1.0 | 0.2 | 92.4 | 1260 |

The Brookfield viscosity of the 2-in-1 shampoo composition containing the polymer of Example 1 and Polyquaternium-7 (F5-3) was higher than that of the analogous shampoo composition containing CA SF-1 and Polyquaternium-7 (F5-5) at the same amount of polymer content. A higher visual clarity was obtained for shampoo compositions containing the polymer of Example 1 and Polyquaternium-7 (F5-3) than for an analogous shampoo composition containing CA SF-1 and Polyquaternium-7 (F5-5), at the same amount of polymer content.

Example F6

The performance of the polymer of Example 5 was evaluated in a series of analogous aqueous liquid hand soap compositions, each comprising 2.5 pbw of the polymer of Example 5 per 100 pbw of the hand soap composition and a mixture comprising ethoxylated (2 moles ethylene oxide per mole) sodium laureth (SLES) and cocamidopropylbetaine ("CAPB") in a ratio of 4.5 pbw SLES per 1 pbw CAPB, in the relative amounts set forth in TABLE XV below, as pbw of the mixture per 100 pbw of the hand soap composition. Viscosity was measured using Brookfield DVD-I or DVD VII viscometer at 10 rpm as described above in regard to Examples F1-F11, yield strength was determined as described above in regard to Examples F1-F11, and transmittance at 600 nanometers was determined as described above in regard to Examples F1-F11. The results are set forth in TABLE XVI below as viscosity (in milliPascal seconds ("mPa·s"), yield strength (in Pascals ("Pa"), and transmittance at 600 nm (as % transmittance) for each of the compositions.

TABLE XVI

| | Surfactant Content (pbw SLES + CAPB surfactant mixture/100 pbw composition) | | | |
|---|---|---|---|---|
| | 7.0 | 9.0 | 11.0 | 13.0 |
| Brookfield Viscosity (mPa·s) | 23240 | 14960 | 13760 | 16280 |
| Yield stress (Pa) | 2.7 | 2.2 | 1.3 | 1.2 |
| Transmittance at 600 nm (%) | 98.0 | 99.5 | 98.4 | 95.4 |

The polymer of Example 5 exhibited good thickening efficiency within the range of surfactant content tested, with higher thickening efficiency at lower surfactant content.

A variety of particles, beads, and capsules with different density and diameter were added in analogous compositions comprising 2.5 pbw of the polymer of Example 5 per 100 pbw of the respective composition. The compositions were found to be stable after 3 months storage at 45° C. All of the compositions exhibited a high degree of clarity (greater than or equal to 95% transmittance) over the entire range of surfactant content tested.

Example F7

The foaming performance of analogous liquid hand soap compositions, each comprising, based on 100 pbw of the hand soap composition, 9 pbw SLES, 2 pbw CAPB, 2.85 pbw NaCl, and 0 or 2.5 pbw of the active polymer of Example 5 or of SF-1 polymer or 3.2 pbw of SF-1 polymer, was evaluated. Foam volume and stability were evaluated as follows. The test compositions were diluted to 10% with water. A 20 ml aliquot of diluted solution was introduced into plastic syringes set on horizontal fixed metallic bar. Just above it, a mobile metallic bar emptied the syringes, with the liquid falling into 100 ml glass cylinders, each containing 10 ml of the same diluted solution. The resulting high speed falling jet produced foam, which volume level is monitored from 5 seconds to 5 min after its formation. Foam firmness was evaluated by generating foams having bubbles sizes of from 0.5 to 1 mm at a liquid content of 3.6-3.9% through continuous introduction of a controlled nitrogen flow in the surfactant solution pumped at a controlled pressure in a glass column filled with glass beads having a nominal diameter of 2 mm. The foam generated is collected in a 50 ml Schott Duran beaker of volume 49.9 cm$^3$ and put on a balance. A tester comprising 0.7 mm thick stainless steel, driven through a piezoelectric crystal, acts on the foam and generates a force registered by the balance, which can be related to foam elasticity or firmness. Results are set forth below in TABLE XVII, parts A and B, as foam volume over time (in milliliters ("ml")) and foam firmness (in milliNewtons ("mN") with the standard deviation for each value.

TABLE XVII parts A and B

A. Foam Volume (ml)

| | Polymer of Ex 5 (2.5 pbw/100 pbw) | | SF-1 Polymer (2.5 pbw/100 pbw) | |
|---|---|---|---|---|
| time (min) | Foam volume (ml) | Std. deviation | Foam volume (ml) | Std. deviation |
| 0 | 74.7 | 1.0 | 72.7 | 1.6 |
| 1 | 68.5 | 2.1 | 65.5 | 0.7 |
| 3 | 62.3 | 1.1 | 60 | 0.0 |

B. Foam Firmness (mN)

| | Amplitude/mN | Std. deviation |
|---|---|---|
| No polymer | 12.89 | 0.24 |
| Polymer of Ex 5 (2.5 pbw/100 pbw) | 15.35 | 0.29 |
| SF-1 (2.5 pbw/100 pbw) | 13.76 | 0.14 |
| SF-1 (3.2 pbw/100 pbw) | 15.73 | 0.12 |

The reference system with no polymer exhibited low foam firmness. Introduction of either the polymer of Example 5 or the comparative polymer increased foam firmness. The increase in foam firmness was much larger for a given amount of polymer with the polymer of Example 5, with more of the comparative polymer being required to reach a given level of foam firmness.

Example F8

The facial scrub composition of Example F8 was prepared as follows. The polymer latex of Example 5 was added to deionized water under moderate agitation. Disodium laureth sulfosuccinate ("DLSS", as Mackanate EL) was then added, followed by slow addition of a sodium hydroxide solution (15%) to the mixture so as to reach a pH of about 6.5. Sodium cocoamphoacetate ("CAMA" as Miranol Ultra C-32) was then added, followed by preservative. The pH of the composition was then adjusted to 6.5 with a solution of citric acid (15%). Florapearls Jojoba STD evergreen beads were then added under slow agitation. Compositions are given in TABLE XVIII A below, for each material, as pbw active material per 100 pbw of the facial scrub composition. Viscosity was measured using Brookfield DVD-I or DVD VII viscometer at 10 rpm as described above in regard to Examples F1-F11, yield strength was determined as described above in regard to Examples F1-F11. The results are set forth below in TABLE XVIII B, as viscosity (in centiPoise ("cP"), yield strength (in Pascals ("Pa").

TABLE XVIII

| Material | Amount (pbw per 100 pbw) |
|---|---|
| A. | |
| Polymer of Ex 5 | 2.5 |
| CAMA | 3.90 |
| DLSS | 3.30 |
| Florapearls Jojoba STD evergreen beads | 0.25 |

TABLE XVIII-continued

| Material | Amount (pbw per 100 pbw) |
|---|---|
| Preservative | 0.05 |
| NaOH (15%) | q.s |
| Citric Acid (15%) | q.s |
| Water | to 100 |
| B. | |
| pH | 6.5 |
| Viscosity (cP) | 9320 |
| Yield Stress (Pa) | 1.4 |

The composition was found to be stable after 3 months storage at 45° C.

Examples F9-1 to F9-7 and Comparative Examples CF9-1 and CF9-2

Each of the "sulfate free" facial scrub compositions of Examples F9-1 to F9-7 and Comparative Examples CF9-1 and CF9-2 was made by combining a mixture of disodium laureth sulfosuccinate ("DLSS") and cocamidopropyl hydroxysultaine ("CAPHS") in the pbw:pbw ratio given in the TABLE XVIII, parts A and B, below, and either the polymer of Example 5 or a comparative polymer (SF-1), in the amount given in the TABLE XVIII, parts A and B, below, based on 100 pbw of the facial scrub composition, as pbw of surfactant mixture and pbw of polymer. This sulfate free surfactant system cannot be thickened through standard salt addition. Viscosity was measured using Brookfield DVD-I or DVD VII viscometer at 10 rpm as described above in regard to Examples F1-F11, yield strength was determined as described above in regard to Examples F1-F11, and transmittance at 600 nanometers was determined as described above in regard to Examples F1-F11. The results are set forth below in TABLE XIX, parts A and B, as viscosity (in centiPoise ("cP"), yield strength (in Pascals ("Pa"), and transmittance at 600 nm (as % transmittance) for each of the compositions.

TABLE XIX

Parts A and B

A. Viscosity, Yield, Transmittance for Polymer of Example 5

| Ex# | Surfactant mixture (pbw/100 pbw) | Surfactant ratio (pbw DLSS/pbw CAPHS) | Polymer of Ex 5, (pbw/100 pbw) | pH | Viscosity (cP) | Yield Stress (Pa) | Transmittance 600 nm (%) |
|---|---|---|---|---|---|---|---|
| F9-1 | 9 | 3 | 2.5 | 6.5 | 6240 | 1.1 | 94.3 |
| F9-2 | 11 | 3 | 2.5 | 6.5 | 6300 | 1.1 | 93.5 |
| F9-3 | 11 | 3 | 2.75 | 6.5 | 11100 | 1.9 | 95.5 |
| F9-4 | 11 | 3 | 3.0 | 6.5 | 17240 | 2.3 | 96.5 |
| F9-5 | 11 | 1 | 2.5 | 6.5 | 7380 | 1.2 | 93.0 |
| F9-6 | 11 | 1 | 3.0 | 6.5 | 19820 | 2.7 | 94.3 |
| F9-7 | 11 | 0.33 | 2.5 | 6.6 | 7440 | 1.3 | 81.9 |

B. Viscosity, Yield, and Transmittance for Comparative Polymer

| Ex# | Surfactant mixture (pbw/100 pbw) | Surfactant ratio (pbw DLSS/pbw CAPHS) | SF-1 polymer (pbw/100 pbw) | pH | Viscosity (cP) | Yield Stress (Pa) | Transmittance at 600 nm (%) |
|---|---|---|---|---|---|---|---|
| CF9-1 | 11 | 3 | 2.5 | 6.6 | 4280 | 2.1 | 93.3 |
| CF9-2 | 11 | 3 | 2.76 | 6.6 | 6300 | 3.0 | 91.5 |

The comparative polymer exhibited lower thickening efficiency and lower transmittance compared to the polymer of Example 5 in the context of the sulfate free DLSS/CAPHS surfactant system.

Examples F10-1 and F10-2 and Comparative Examples CF10-1 to CF10-4

The performance of 2-in-1 shampoo/conditioner compositions of Example F10 and Comparative Examples CF10-1 to CF10-4, comprising, based on 100 pbw of the shampoo/conditioner composition 12.5 pbw SLES 2.5 pbw CAPB and 1.5 pbw NaCl, 0.3 pbw active guar hydroxypropyltrimonium chloride (Jaguar C-14S), 2 pbw active submicronic dimethicone emulsion (Mirasil DME-0.6, 65 wt % active silicone content), and either the polymer of Example 5, a first comparative polymer, SF-1, or second comparative polymer (crosslinked acrylic polymer, Carbopol® C 980 (Lubrizol Corporation, ("C 980")) or no polymer, each in the amount indicated, as pbw per 100 pbw of the shampoo/conditioner composition, in TABLE XX below, was evaluated. In each case, the pH of the composition was adjusted at 6.5. The final polymer dosage was defined by adjusting the formulation viscosity to a target value of approx 10.000 cP. Viscosity was measured using Brookfield DVD-I or DVD VII viscometer at 10 rpm as described above in regard to Examples F1-F11, yield strength was determined as described above in regard to Examples F1-F11, and transmittance at 600 nanometers was determined as described above in regard to Examples F1-F11. The results are set forth below in TABLE XX, as viscosity (in centiPoise ("cP"), yield strength (in Pascals ("Pa"), and transmittance at 600 nm (as % transmittance) for each of the shampoo/conditioner compositions.

TABLE XX

| Ex# | Type of Polymer | Polymer (pbw/100 pbw) | Viscosity (cP) | Yield Stress (Pa) | Transmittance at 600 nm (%) |
|---|---|---|---|---|---|
| F10-1 | Polymer of Ex 5 | 0.35 | 10600 | 0.12 | 19.6 |
| CF10-1 | SF-1 Polymer | 0.90 | 11240 | 0.09 | 23.1 |
| CF10-2 | C 980 Polymer | 0.30 | 11800 | 0.10 | 1.55 |
| CF10-3 | No polymer (1.5 pbw NaCl/100 pbw) | 0.0 | 4120 | ~0 | 34.7 |
| CF10-4 | No polymer (1.75 pbw NaCl/100 pbw) | 0.0 | 9200 | ~0.02 | 21.6 |

Silicone deposition yield was measured for compositions analogous to those described in TABLE XX above, except with the NaCl content adjusted to 1.75 wt %, according to following procedure. Silicone oil deposition is evaluated on virgin hair (Virgin Medium Brow Caucasian hair from IHIP) for each formulation, by washing using 4.5 g of hair with dose of shampoo of approximately 450 mg. The silicone oil deposited on hair is extracted with tetrahydrofuran and the deposition yield is measured with gas chromatography. The amount of active polymer, as wt % of the composition, and results are set forth below in TABLE XX, as Silicone Deposition Yield in %.

TABLE XXI

| Ex# | Type of Polymer | Polymer, (pbw/100 pbw) | Silicone Deposition Yield (%) |
|---|---|---|---|
| CF10-5 | No polymer | 0 | 36.8 |
| F10-2 | Ex 5 | 0.35 | 34.1 |
| CF10-6 | SF-1 | 0.9 | 19.9 |
| CF10-7 | C 980 | 0.3 | 34.9 |

The C 980 polymer and polymer of Ex 5 were each found to have minor impact on silicone deposition yield, while the CA SF-1 polymer was found to reduce silicone deposition yield.

Examples F11-1 and F11-2 and Comparative Example CF11

The hair gel compositions of Examples F11-1, F11-2 and Comparative Example CF11 were made as follows. To form phase A, aqueous 5% 2-amino-2-methyl-1-propanol (as Amp-95) and ethylenediamine tetracetic acid (EDTA) were added to Part 1 of the water in a mixing vessel and mixed until uniform, and then vinyl pyrrolidone/vinyl acetate (as PVP/VA W 635), glycerin, and the preservative (DMDM Hydantoin) were added to the mixing vessel and mixed until uniform. In a separate vessel, the polymer was added to part 2 of the water and mixed until uniform. Phase A was slowly added to phase B and mixed until the mixture became clear. The pH was then adjusted to 7.5-8.5, if necessary. The amounts of the materials used, in grams ("g"), and the active content of such materials, as wt % of such materials, are given in TABLE XXII A below. The appearance, the pH, and the viscosity, in centiPoise ("cP"), as measured using a Brookfield RV5 viscometer at 2.5 revolutions per minute, were evaluated for each of the compositions and are reported, along with the amount of active polymer, as pbw polymer per 100 pbw of the hair gel composition, in TABLE XXII B below.

TABLE XXII

A.

| Phase | Material | Active content of material (wt %) | Ex F11-1 Amount of material (g) | Ex F11-2 Amount of material (g) | Ex CF11 Amount of material (g) |
|---|---|---|---|---|---|
| A | DI water, Part 1 | | 51.50 | 51.10 | 94.60 |
| | AMP-95 | 95 | 0.60 | 0.7 | 0.2 |
| | EDTA | 100 | 0.50 | 0.5 | 0.7 |
| | PVP/VA W 635 | 50 | 2.00 | 2.2 | 2 |
| | Glycerin | 100 | 2.60 | 2.1 | 2.1 |
| | Preservative | 100 | 0.50 | 0.5 | 1 |
| B | DI water, Part 2 | | 40.00 | 40 | 0 |
| | Aqueous Solution of Polymer of Ex 6 | 28.6 | 0 | 6.00 | 0 |
| | Aqueous Solution of Polymer of Ex 5 | 28 | 6.10 | 0 | 0 |

B.

| | Ex F11-1 | Ex F11-2 | Ex CF11 |
|---|---|---|---|
| Polymer content (pbw per 100 pbw) | 1.65 | 1.66 | 0 |
| Appearance | Hazy/Transparent | Hazy/Transparent | Clear, Water Thin |
| pH | 7.53 | 8.15 | 8.35 |
| Viscosity (cP) | 97000 | 142,000 | 160 |

Examples F12-1 and F12-2 and Comparative Example CF12

The hair gel compositions of Examples F12-1 and F12-2, and Comparative Example CF12 were made as follows. To form Phase A, aqueous 5% 2-amino-2-methyl-1-propanol (Amp –95) and ethylenediamine tetracetic acid (EDTA) were added to Part 1 of the water in a mixing vessel and mixed until uniform and then the conditioner (an aqueous mixture of Polyquaternium-II, VP/VA Copolymer butoxyethanol, soyamide DEA, PPG-30, cetyl ether, oleth-30 phosphate, panthenol, modimethicone, trideceth-12, cetrimonium chloride, PEG-12 dimethicone, and DMDM Hydantoin, as Mackconditioner LCB II) was added and mixed until uniform. In a separate vessel, the polymer was added to part 2 of the water and mixed until uniform. Phase A was then slowly added to phase B and mixed until the mixture became clear. The pH was then adjusted to 7.5-8.5, if necessary. The amounts of the materials used, in grams ("g"), and the active content of such materials, as wt % of such materials, are given in TABLE XXIII A below. The appearance, the pH, and the viscosity in centiPoise ("cP"), as measured using a Brookfield RV6 viscometer at 0.5 revolutions per minute, were evaluated for each of the compositions and are reported, along with the amount of active polymer, as pbw polymer per 100 pbw of the hair gel composition, in TABLE XXIII B below.

TABLE XXIII

A.

| Phase | Material | Active content of material (wt %) | Ex F12-1 Amount of material (g) | Ex F12-2 Amount of material (g) | Ex CF12 Amount of material (g) |
|---|---|---|---|---|---|
| A | DI water, Part 1 |  | 12.80 | 12.70 | 59.40 |
|  | AMP-95 | 95 | 0.80 | 0.70 | 0.10 |
|  | EDTA | 100 | 0.60 | 0.50 | 0.40 |
|  | conditioner | 50 | 40.00 | 40.00 | 40.70 |
| B | DI water, Part 2 |  | 40.00 | 40.00 | 0.00 |
|  | Aqueous Solution of Polymer of Ex 6 | 28.6 | 6.10 | 0.00 | 0.00 |
|  | Aqueous Solution of Polymer of Ex 5 | 28 | 0.00 | 6.40 | 0.00 |

B.

|  | Ex F12-1 | Ex F12-2 | Ex CF12 |
|---|---|---|---|
| Polymer content (pbw per 100 pbw) | 1.74 | 1.79 | 0 |
| Appearance | Turbid/Cream colored | Turbid/Cream colored | Turbid/Cream colored |
| pH | 8.46 | 8.41 | 8.31 |
| Viscosity (cP) | 1750000 cps | 900000 cps | 0 cps |

Examples F13-1 to F13-4 and Comparative Example CF13

The laundry detergent compositions of Examples F13-1 to F13-4 and Comparative Example CF13 were made as follows. ¾ of the deionized ("DI") water, part 1, was introduced to the beaker and heated to 55° C. Sodium hydroxide and coconut fatty acid were then added and allowed to saponify (saponification took about 45 mins). Aqueous 61% sodium dodecyl benzene sulfonate (as Rhodacal SS60/A, "SDBS") was then added and mixed. Aqueous 90% linear alcohol ethoxylate (as Rhodsurf L 7/90) was then added and mixed. The pH was then adjusted with citric acid to 7.6. Propylene glycol, aqueous 70% sodium laureth sulfate (as Rhodapex ESB-70/A2, "SLS"), and aqueous 33% sodium diethylenetriamine pentakis(methylenephosphonate) (as Briquest 543-33S, "SDTPMP") were then added and mixed until uniform. The mixture was then cooled to 35° C. Dye, fragrance, polymer, and rest of the water were then added and mixed until uniform. The amounts of the materials used, in grams ("g"), and the active content of such materials, as wt % of such materials, are given in TABLE XXIV A below. The pH, the appearance, and the viscosity, in centiPoise ("cP"), as measured using a Brookfield LV3 viscometer at 60 revolutions per minute, were evaluated for each of the compositions and are reported, along with the amount of active polymer, the as pbw polymer per 100 pbw of the hair gel composition, in TABLE XXIV B below.

TABLE XXIV

| Material | Active content of material (wt %) | Ex F13-1 Amount of material (g) | Ex F13-2 Amount of material (g) | Ex F13-3 Amount of material (g) | Ex F13-4 Amount of material (g) | Ex CF13 Amount of material (g) |
|---|---|---|---|---|---|---|
| A. | | | | | | |
| DI water, Part 1 |  | 29.09 | 29.09 | 29.09 | 29.09 | 29.09 |
| Sodium Hydroxide | 50 | 5.41 | 5.41 | 5.41 | 5.41 | 5.41 |
| Coconut Fatty Acid | 100 | 7.50 | 7.50 | 7.50 | 7.50 | 7.50 |
| SDBS | 61 | 14.75 | 14.75 | 14.75 | 14.75 | 14.75 |
| Linear alcohol ethoxylate | 90 | 11.11 | 11.11 | 11.11 | 11.11 | 11.11 |
| Citric Acid | 100 | 2.01 | 2.01 | 2.01 | 2.01 | 2.01 |
| Propylene Glycol | 100 | 6.50 | 6.50 | 6.50 | 6.50 | 6.50 |
| SLS | 70 | 7.14 | 7.14 | 7.14 | 7.14 | 7.14 |
| SDTPMP | 33 | 3.03 | 3.03 | 3.03 | 3.03 | 3.03 |
| Di Water, Part 2 |  | 9.56 | 9.56 | 9.56 | 9.56 | 9.56 |

TABLE XXIV-continued

| Material | Active content of material (wt %) | Ex F13-1 Amount of material (g) | Ex F13-2 Amount of material (g) | Ex F13-3 Amount of material (g) | Ex F13-4 Amount of material (g) | Ex CF13 Amount of material (g) |
|---|---|---|---|---|---|---|
| FD&C Blue #1 | 0.25 | 0.40 | 0.40 | 0.40 | 0.60 | 0.40 |
| Fragrance | 100 | 1.20 | 1.20 | 1.40 | 1.20 | 1.30 |
| NaOH (50%) | 50 | 0.10 | 0.10 | 0.20 | 0.30 | 0.00 |
| Di Water, Part 3 | | 0.00 | 0.00 | 0.00 | 0.00 | 6.30 |
| Aqueous Solution of Polymer of Ex 6 | 28.6 | 7.60 | — | — | — | — |
| Aqueous Solution of Polymer of Ex 7 | 28.57 | — | — | 7.40 | — | — |
| Aqueous Solution of Polymer of Ex 8 | 28.1 | — | — | — | 7.60 | — |
| Aqueous Solution of Polymer of Ex 5 | 28 | — | 7.40 | — | — | — |
| B. | | | | | | |
| pH | | 7.8 | 7.7 | 7.8 | 8.0 | 8.1 |
| Polymer content (pbw per 100 pbw) | | 2.1 | 2.0 | 2.0 | 2.0 | 0 |
| Appearance | | Turbid/dark blue | Turbid/blue | Turbid/blue | Turbid/blue | Clear/blue/water thin |
| Viscosity (cP) | | 1,100 | 600 | 800 | 900 | 200 |

Examples F14-1 and F 14-2 and Comparative Example CF14

The bleach compositions of Examples F14-1 and F14-2 and Comparative CF14 were made as follows. The polymer was added to water and mixed until uniform, aqueous 6% sodium hypochlorite was then added and mixed until uniform, and aqueous 47.5% dihydroxyethyl tallow glycinate was then added and mixed until uniform. The amounts of the materials used, in grams ("g"), and the active content of such materials, as wt % of such materials, are given in TABLE XXIV A below. The pH and the viscosity, in centiPoise ("cP"), as measured using a Brookfield RV5 viscometer at 10 revolutions per minute, were evaluated for each of the compositions and are reported, along with the amount of active polymer, the as pbw polymer per 100 pbw of the bleach composition, in TABLE XXV B below.

TABLE XXV

A.

| Material | Active content of material (wt %) | Ex F14-1 Amount of material (g) | Ex F14-2 Amount of material (g) | Ex CF14 Amount of material (g) |
|---|---|---|---|---|
| DI water Part 1 | | 86.00 | 86.00 | 86.00 |
| sodium hypochlorite | 6 | 10.00 | 10.00 | 10.00 |
| dihydroxyethyl tallow glycinate | 47.5 | 2.00 | 2.00 | 2.00 |
| Sodium Hydroxide | 50 | 0.00 | 0.00 | 0 |
| Aqueous solution of Polymer of Ex 6 | 28.6 | 5.30 | 0 | 0 |
| Aqueous solution of Polymer of Ex 5 | 28 | 0.00 | 2.1 | 0 |

B.

| | Ex F14-1 | Ex F14-2 | Ex CF14 |
|---|---|---|---|
| Polymer, content (pbw per 100 pbw) | 1.47 | 0.59 | 0 |
| Appearance | Turbid/white | Phase Separated | Phase Separated |
| pH | 9.96 | — | — |
| Viscosity | 11,600 cps | — | — |

Examples F 15-1 and F 15-2 and Comparative Example CF15

The bleach compositions of Examples F 15-1 and F 15-2, and Comparative Example CF 15 were made as follows. Polymer and aqueous 47.5% dihydroxyethyl tallow glycinate (as Mirataine™) were added to the Clorox Clean-Up™ cleaner (an aqueous mixture of sodium hypochlorite, sodium hydroxide, and proprietary ingredients) and mixed until uniform, and then the pH was adjusted to 11 to 12. The amounts of the materials used, in grams ("g"), and the active content of such materials, as wt % of such materials, are given in TABLE XXVI A below. The pH, the appearance, and the viscosity, in centiPoise ("cP"), as measured using a Brookfield RV5 viscometer at 2.5 revolutions per minute, were evaluated for each of the compositions and are reported, along with the amount of active polymer, the as pbw polymer per 100 pbw of the bleach composition, in TABLE XXVI B below.

TABLE XXVI

A.

| Material | Active content of material (wt %) | Ex F15-1 Amount of material (g) | Ex F15-2 Amount of material (g) | Ex CF15 Amount of material (g) |
|---|---|---|---|---|
| Clorox Clean-up ™ cleaner | 100 | 100.00 | 100.00 | 100 |
| dihydroxyethyl tallow glycinate | 47.5 | 2.00 | 2.00 | 2 |
| Sodium Hydroxide | 50 | 0.00 | 0.00 | 0 |
| Aqueous solution of Polymer of Ex 6 | 28.6 | 7.10 | 0 | 0 |
| Aqueous solution of Polymer of Ex 5 | 28 | 0.00 | 7.7 | 0 |

B.

| | Ex F15-1 | Ex F15-2 | Ex CF15 |
|---|---|---|---|
| Polymer, content (pbw per 100 pbw) | 1.86 | 1.97 | 0 |
| Appearance | Turbid/white | Turbid/white | Turbid/Yellow |
| pH | 12.9 | 12.6 | 12.7 |
| Viscosity (cP) | 144,000 | 99,500 | 40 |

Examples F 16-1 and F16 2 and Comparative Examples CF16-1 and CF16-2

The bleach compositions of Examples F 16-1, F16 2 and Comparative Examples CF 16-1 and CF 16-2 were made as follows. Polymer was added to the water and mixed until uniform. Aqueous 11.5% sodium hypochlorite was then added and mixed until uniform and then aqueous 47.5% dihydroxyethyl tallow glycinate (as Mirataine™) was added and mixed until uniform. Adjust pH to 11 to 12. The amounts of the materials used, in grams ("g"), and the active content of such materials, as wt % of such materials, are given in TABLE XXVII A below. The pH, the amount of polymer, wt % of the composition, the appearance, and the viscosity, in centiPoise ("cP"), as measured using a Brookfield RV5 viscometer at 10 revolutions per minute, were evaluated for each of the compositions and are reported in TABLE)(XVII B below.

TABLE XXVII

A.

| Material | Active content of material (wt %) | Ex F16-1 Amount of material (g) | Ex F16-2 Amount of material (g) | Ex CF16-1 Amount of material (g) | Ex CF16-2 Amount of material (g) |
|---|---|---|---|---|---|
| DI water Part 1 | | 36.50 | 36.60 | 43.5 | 50 |
| Sodium Hypochlorite | 11.5 | 52.20 | 52.20 | 52.2 | 50 |
| dihydroxyethyl tallow glycinate | 47.5 | 4.20 | 4.20 | 4.2 | — |
| Sodium Hydroxide | 50 | 1.00 | 2.00 | 0 | — |
| Aqueous Solution of Polymer of Ex 6 | 28.6 | 0.00 | 7 | 0 | — |
| Aqueous Solution of Polymer of Ex 5 | 28 | 7.30 | 0 | 0 | — |

B.

| | Ex F16-1 | Ex F16-2 | Ex CF16-1 | Ex CF16-2 |
|---|---|---|---|---|
| Polymer, content (pbw per 100 pbw) | 2.02 | 1.96 | 0 | 0 |
| Appearance | Phase Separated | turbid/yellow tint | Phase Separated | Clear/yellow |
| pH | — | 31800 cps | — | 40 cps |
| Viscosity (cP) | — | 12.6 | — | 12.4 |

What is claimed is:

1. A polymer made by copolymerization of a mixture of polymerizable monomers, said polymerizable monomers which copolymerize to form the polymer comprising:

(a) one or more first monomers each independently selected from monomers according to structure (XIII):

(XIII)

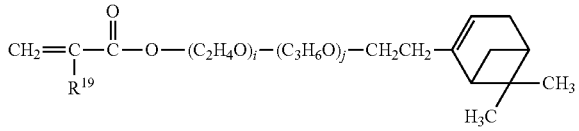

wherein:

$R^{19}$ is H or methyl, i is an integer of from 10 to 40, and j is an integer of from 1 to 20, (b) one or more second monomers copolymerizable with the first monomer, wherein: the one or more second monomers are each independently selected from monomers according to structure (XX):

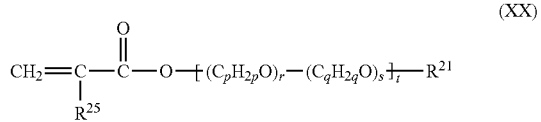
(XX)

wherein
$R^{21}$ is linear $(C_5\text{-}C_{50})$alkyl,
$R^{25}$ is methyl or ethyl
p and q are independently integers of from 2 to 5,
each r is independently an integer of from 1 to about 80,
each s is independently an integer of from 0 to about 80, and
t is an integer of from 1 to about 50, provided that the product obtained by multiplying the integer t times the sum of r+s is from 2 to about 100, and
(c) one or more third monomers each independently selected from monocarboxylic acid monomers according to structure (XXII):

(XXII)

wherein:
$R^{31}$ is a moiety that comprises a carboxylic acid, sulfonic acid, or phosphoric acid group,
$R^{32}$ is absent or is a bivalent linking group, and
$R^{34}$ is a moiety having a site of ethylenic unsaturation, and
(d) one or more fourth monomers each independently selected from compounds according to structure (XXIV):

(XXIV)

wherein:
$R^{41}$ is alkyl, hydroxyalkyl, alkoxyalkyl, cycloalkyl, aryl, aralkyl, or aryloxy,
$R^{42}$ is absent or is a bivalent linking group, and
$R^{43}$ is a moiety having a site of ethylenic unsaturation.

2. The polymer of claim 1, wherein:
p=2
r is an integer of from 10 to 40,
s=0, and
t=1.

3. The polymer of claim 1, wherein:
(a)
  i is an integer of from 15 to 30,
  j is an integer from 2 to 10,
(b)
  p=2,
  r is an integer of from 10 to 50,
  s=0,
  t=1,
(c) $R^{31}$ is a carboxylic acid group, and
(d) $R^{41}$ is $(C_1\text{-}C_{12})$alkyl.

4. The polymer of claim 1, wherein $R^{21}$ is linear $(C_{16}\text{-}C_{22})$ alkyl, $R^{25}$ is methyl or ethyl, p=2, s=0, and t=1.

5. The polymer of claim 1, wherein the polymer is a non-crosslinked polymer.

6. The polymer of claim 1, wherein the polymer is a crosslinked polymer.

7. The polymer of claim 1, wherein:
$R^{19}$ is H or methyl,
i is an integer of from 15 to 30, and
j is an integer of from 2 to 10.

8. The polymer of claim 1, wherein:
the one or more second monomers comprise a mixture of second monomers, wherein, in each case:
$R^{21}$ is selected from linear $C_{16}$ alkyl, linear $C_{18}$ alkyl, and linear $C_{22}$ alkyl groups,
p=2
r is an integer of from 10 to 50,
s=0, and
t=1.

9. The polymer of claim 1, wherein $R^{31}$ is a carboxylic acid group.

10. The polymer of claim 1, wherein $R^{41}$ is $(C_1\text{-}C_6)$alkyl.

11. The polymer of claim 1, wherein:
(a)
  i is an integer of from 15 to 30,
  j is an integer of from 2 to 10,
(b) the one or more second monomers comprise a mixture of second monomers, wherein, in each case, $R^{21}$ is selected from linear $C_{16}$ alkyl, linear $C_{18}$ alkyl, and linear $C_{22}$ alkyl groups,
  p=2,
  r is an integer of from 10 to 50,
  s=0,
  t=1,
(c) the one or more third monomers comprise at least one monocarboxylic monomer selected from acrylic acid and methacrylic acid, and
(d) the one or more fourth monomers comprise at least one monomer selected from $(C_1\text{-}C_6)$alkyl acrylic esters and $(C_1\text{-}C_6)$alkyl methacrylic esters.

12. The polymer of claim 11, wherein the polymer is a crosslinked polymer.

13. A process for making a polymer of claim 1, comprising polymerizing a mixture of monomers said mixture comprising:
(a) the one or more first monomers,
(b) the one or more second monomers,
(c) the one or more third monomers, and
(d) the one or more fourth monomers.

14. A composition comprising a liquid medium and one or more polymers according claim 1.

15. The composition of claim 14, further comprises one or more surfactants.

16. The composition of claim 14, wherein the composition is an aqueous latex coating composition that further comprises a polymer latex.

17. The composition of claim 14, wherein the composition is a personal care composition.

18. The composition of claim 17, wherein the composition further comprises one or more surfactants.

19. The composition of claim 17, wherein the composition is substantially free or free of sulfate surfactant compounds.

20. The composition of claim 17, wherein the composition further comprises one or more personal care benefit agents.

21. The composition of claim 17, wherein the composition comprises an amount of polymer effective to impart a yield strength of greater than 0 Pa to the composition.

22. The composition of claim 17, wherein the composition exhibits a clear, transparent visual appearance.

23. The composition of claim 17, wherein the composition comprises an amount of polymer effective to impart a yield strength of greater than 1 Pa to the composition and the composition further comprises suspended particles of one or more solid, liquid, or gas that are insoluble or are only partly soluble in the personal care composition.

24. The composition of claim 14, wherein the composition is home care composition or institutional or industrial care composition.

25. The composition of claim 24, wherein the composition further comprises one or more surfactants and, optionally, one or more additives selected from builders, bleaching agents, acids, bases, or abrasives, antibacterial agents, fungicides, enzymes, and opacifing agents.

26. A composition comprising a liquid medium and one or more polymers according claim 1.

27. The polymer of claim 1, wherein the polymerizable monomers consist of:
(a) the one or more first monomers,
(b) the one or more second monomers,
(c) the one or more third monomers, and
(d) the one or more fourth monomers;
wherein the polymer is optionally crosslinked polymer by optional crosslinker monomer.

28. The polymer of claim 27, wherein:
$R^{19}$ is H or methyl,
i is an integer of from 15 to 30, and
j is an integer of from 2 to 10.

29. The polymer of claim 27, wherein:
the one or more second monomers consist of a mixture of second monomers, wherein, in each case:
$R^{21}$ is selected from linear $C_{16}$ alkyl, linear $C_{18}$ alkyl, and linear $C_{22}$ alkyl groups,
p=2
r is an integer of from 10 to 50,
s=0, and
t=1.

30. The polymer of claim 27, wherein $R^{31}$ is a carboxylic acid group.

31. The polymer of claim 27, wherein $R^{41}$ is $(C_1-C_6)$alkyl.

32. The polymer of claim 27, wherein:
(a) $R^{19}$ is H or methyl,
i is an integer of from 15 to 30,
j is an integer of from 2 to 10,
(b) the one or more second monomers are a mixture of second monomers, wherein, in each case, $R^{21}$ is selected from linear $C_{16}$ alkyl, linear $C_{18}$ alkyl, and linear $C_{22}$ alkyl groups,
p=2,
r is an integer of from 10 to 50,
s=0,
t=1,
(c) the one or more third monomers are at least one monocarboxylic monomer selected from acrylic acid and methacrylic acid, and
(d) the one or more fourth monomers are at least one monomer selected from $(C_1-C_6)$alkyl acrylic esters and $(C_1-C_6)$alkyl methacrylic esters.

33. The polymer of claim 27, wherein the crosslinker monomer is in the mixture and selected from the group consisting of:
polyfunctional monomers containing multiple reactive groups selected from epoxide groups, isocyanate groups, and hydrolyzable silane groups, polyunsaturated crosslinker monomers selected from polyunsaturated aromatic monomers, divinylbenzene, divinyl naphthalene, and trivinylbenzene, polyunsaturated alicyclic monomers, 1,2,4-trivinylcyclohexane, di-functional esters of phthalic acid, diallyl phthalate, polyunsaturated aliphatic monomers, dienes, trienes, and tetraenes, including isoprene, butadiene, 1,5-hexadiene, 1,5,9-decatriene, 1,9-decadiene, 1,5-heptadiene, polyalkenyl ethers, triallyl pentaerythritol, diallyl pentaerythritol, diallyl sucrose, octaallyl sucrose, and trimethylolpropane diallyl ether, polyunsaturated esters of polyalcohols or polyacids selected from 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, poly(alkyleneoxy)glycol di(meth)acrylates, and polyethylene glycol di(meth) acrylate, alkylene bisacrylamides selected from methylenebisacrylamide and propylene bisacrylamide, hydroxy and carboxy derivatives of methylene bis-acrylamide, N,N'-bismethylol methylene bisacrylamide, polyalkyleneglycol di(meth)acrylates selected from ethyleneglycol di(meth)acrylate, diethyleneglycol di(meth)acrylate, and triethyleneglycol di(meth)acrylate, polyunsaturated silanes selected from dimethyldivinylsilane, methyltrivinylsilane, allyldimethylvinylsilane, diallydimethylsilane and tetravinylsilane, polyunsaturated stannanes, tetraallyl tin, diallyldimethyl tin, crosslinker monomers having more than one (meth)acrylic group per molecule selected from allyl methacrylate, ethylene glycol dimethacrylate, butylene glycol dimethacrylate, diallyl pentaerythritol, methylenebisacrylamide, pentaerythritol di-, tri- and tetra-acrylates, divinyl benzene, poly(alkyleneoxy)glycol di(meth)acrylates, polyethylene glycol diacrylates, bisphenol A diacrylates, butanediol dimethacrylate, 2,2-dimethylpropanediol dimethacrylate, ethylene glycol dimethacrylate, phenylene diacrylate, or a mixture thereof.

34. The polymer of claim 1, wherein $R^{43}$ of the one or more fourth monomers is according to structure (XI):

(XI)

wherein
$R^{19}$ is H or $(C_1-C_4)$alkyl.

35. The polymer of claim 1, wherein the one or more fourth monomers are selected from the group consisting of, (meth) acrylic esters, styrene, and ethyl acrylate.

36. The polymer of claim 1, wherein:
(a) the one or more first monomers are selected from monomers according to structure (XIII):

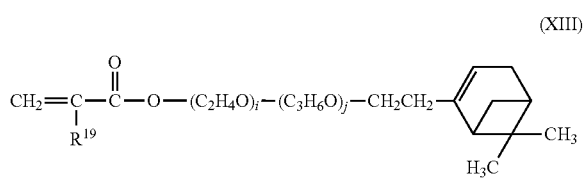

(XIII)

where $R^{19}$ is methyl, i=25, and j=5;
(b) the one or more second monomers are selected from monomers according to structure (XX):

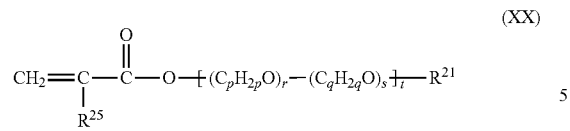
(XX)
wherein R24 is methyl, R21 is a mixture of linear $C_{16}$, linear $C_{18}$, and linear $C_{22}$ alkyl groups, p=2, r=25, s=0, and t=1;
(c) (Elected species) the one or more third monomers is methacrylic acid, and
(d) (Elected species) the one or more fourth monomers is ethyl acrylate.
37. The polymer of claim 36, wherein the polymer is a crosslinked polymer.
* * * * *